(12) United States Patent
Miles et al.

(10) Patent No.: US 11,219,437 B2
(45) Date of Patent: Jan. 11, 2022

(54) SURGICAL ACCESS SYSTEM AND RELATED METHODS

(71) Applicant: NuVasive, Inc., San Diego, CA (US)

(72) Inventors: Patrick Miles, San Diego, CA (US); Scot Martinelli, San Diego, CA (US); Eric Finley, San Diego, CA (US); James E. Gharib, San Diego, CA (US); Allen Farquhar, San Diego, CA (US); Norbert F. Kaula, San Diego, CA (US); Jeffrey J. Blewett, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 326 days.

(21) Appl. No.: 16/659,496

(22) Filed: Oct. 21, 2019

(65) Prior Publication Data

US 2020/0046335 A1    Feb. 13, 2020

Related U.S. Application Data

(60) Continuation of application No. 15/284,797, filed on Oct. 4, 2016, now abandoned, which is a continuation of application No. 14/171,347, filed on Feb. 3, 2014, now Pat. No. 9,468,405, which is a continuation of application No. 13/756,951, filed on Feb. 1, 2013, now Pat. No. 8,696,559, which is a continuation of application No. 13/668,504, filed on Nov. 5, 2012, now Pat. No. 8,550,994, which is a continuation of application No. 13/030,798, filed on Feb. 18, 2011, now Pat. No. 8,303,498, which is a continuation of application No. 12/632,373, filed on Dec. 7, 2009, now Pat. No. 7,892,173, which is a division of application No. 10/789,797, filed on Feb. 27, 2004, now Pat. No. 7,819,801.

(Continued)

(51) Int. Cl.
*A61B 17/02* (2006.01)
*A61B 1/32* (2006.01)
*A61B 5/24* (2021.01)

(52) U.S. Cl.
CPC ........... *A61B 17/0206* (2013.01); *A61B 1/32* (2013.01); *A61B 5/24* (2021.01); *A61B 17/02* (2013.01); *A61B 17/0218* (2013.01); *A61B 2017/0256* (2013.01)

(58) Field of Classification Search
CPC . A61B 17/0206; A61B 17/02; A61B 17/0218; A61B 1/32
See application file for complete search history.

(56) References Cited

U.S. PATENT DOCUMENTS 5,681,265 A * 10/1997 Maeda ..................... A61B 1/32
600/214
5,772,661 A * 6/1998 Michelson ......... A61B 17/1671
606/86 A (Continued)

FOREIGN PATENT DOCUMENTS

WO    WO-0066217 A1 * 11/2000 ........... A61B 5/4893

*Primary Examiner* — Ellen C Hammond

(57) ABSTRACT

A surgical access system including a tissue distraction assembly and a tissue retraction assembly, both of which may be equipped with one or more electrodes for use in detecting the existence of (and optionally the distance and/or direction to) neural structures before, during, and after the establishment of an operative corridor to a surgical target site.

16 Claims, 23 Drawing Sheets

Related U.S. Application Data

(60) Provisional application No. 60/450,806, filed on Feb. 27, 2003.

(56) References Cited

U.S. PATENT DOCUMENTS

| | | | | |
|---|---|---|---|---|
| 5,885,210 A * | 3/1999 | Cox | ............ | A61B 17/0206 600/214 |
| 5,928,139 A * | 7/1999 | Koros | ............ | A61B 17/0206 600/205 |
| 6,139,493 A * | 10/2000 | Koros | ............ | A61B 17/0206 600/213 |
| 6,196,969 B1 * | 3/2001 | Bester | ............ | A61B 17/0206 600/219 |
| 6,916,330 B2 * | 7/2005 | Simonson | ............ | A61B 17/025 606/191 |
| 6,951,538 B2 * | 10/2005 | Ritland | ............ | A61B 17/1757 600/210 |
| 7,582,058 B1 * | 9/2009 | Miles | ............ | A61B 5/296 600/202 |
| 7,691,057 B2 * | 4/2010 | Miles | ............ | A61B 17/025 600/219 |
| 9,788,822 B2 * | 10/2017 | Miles | ............ | A61B 90/37 |
| 2002/0010392 A1 * | 1/2002 | Desai | ............ | A61B 5/743 600/374 |
| 2005/0080320 A1 * | 4/2005 | Lee | ............ | A61B 17/0293 600/214 |
| 2005/0149035 A1 * | 7/2005 | Pimenta | ............ | A61B 1/32 606/86 R |
| 2006/0069315 A1 * | 3/2006 | Miles | ............ | A61B 17/0206 600/219 |
| 2010/0174146 A1 * | 7/2010 | Miles | ............ | A61B 1/32 600/202 |
| 2013/0144127 A1 * | 6/2013 | Miles | ............ | A61B 5/4893 600/202 |
| 2013/0150676 A1 * | 6/2013 | Miles | ............ | A61B 5/389 600/202 |
| 2013/0150678 A1 * | 6/2013 | Miles | ............ | A61B 17/02 600/202 |

* cited by examiner

SURGICAL ACCESS SYSTEM AND RELATED METHODS

CROSS-REFERENCES TO RELATED APPLICATIONS

This application is a continuation of U.S. patent application Ser. No. 15/284,797, filed on Oct. 4, 2016 (currently pending), which is a continuation of U.S. patent application Ser. No. 14/171,347, filed on Feb. 3, 2014 (now U.S. Pat. No. 9,468,405), which is a continuation of U.S. patent application Ser. No. 13/756,951, filed on Feb. 1, 2013 (now U.S. Pat. No. 8,696,559), which is a continuation of U.S. patent application Ser. No. 13/668,504, filed on Nov. 5, 2012 (now U.S. Pat. No. 8,550,994), which is a continuation of U.S. patent application Ser. No. 13/030,798, filed on Feb. 18, 2011 (now U.S. Pat. No. 8,303,498), which is a continuation of U.S. patent application Ser. No. 12/632,373, filed on Dec. 7, 2009 (now U.S. Pat. No. 7,892,173), which is a division of U.S. patent application Ser. No. 10/789,797, filed on Feb. 27, 2004 (now U.S. Pat. No. 7,819,801), which claims priority to U.S. Provisional Patent Application Ser. No. 60/450,806, filed on Feb. 27, 2003, the entire contents of which are hereby expressly incorporated by reference into this disclosure as if set forth fully herein.

BACKGROUND OF THE INVENTION

I. Field of the Invention

The present invention relates generally to systems and methods for performing surgical procedures and, more particularly, for accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called transpsoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which involve detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor.

According to one broad aspect of the present invention, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire, an initial dilator of split construction, and one or more dilators of traditional (that is, non-split) construction for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another simultaneously to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't infringe upon the region of the exiting nerve roots.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior retractor blade is equipped with such a rigid shim element. In an optional aspect, this shim element may be advanced into the disc space after the posterior retractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which serves the dual purpose of preventing post-operative scoliosis and forming a protective barrier (preventing the migration of tissue (such as nerve roots) into the operative field and the inadvertent advancement of instruments outside the operative field).

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, providing one or more strands of fiber optic cable within the walls of the retractor blades such that the terminal (distal) ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
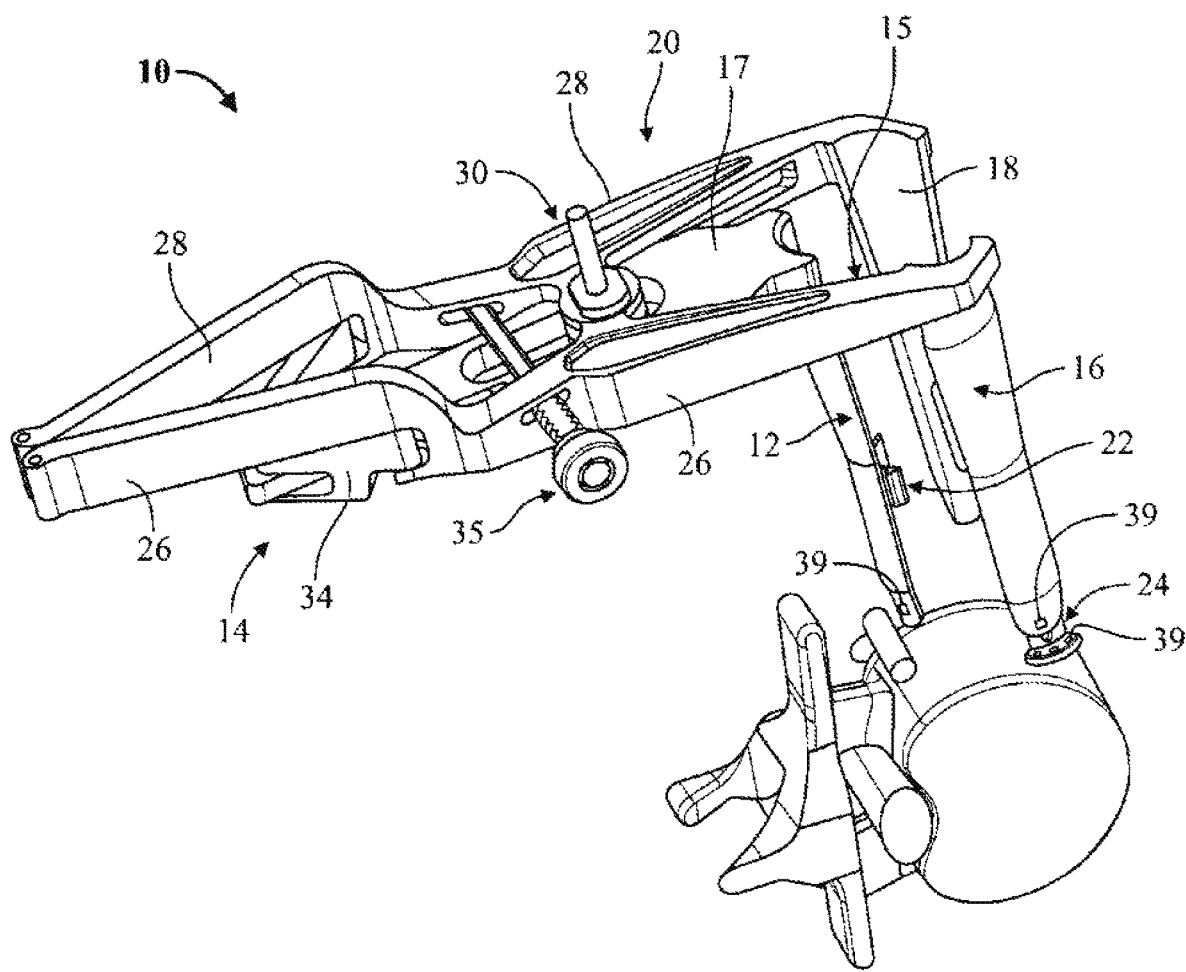
FIG. 1 is a perspective view of a tissue retraction assembly (in use) forming part of a surgical access system according to the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in co-pending and commonly assigned Int'l Patent Application Ser. No. filed Sep. 25, 2002 (claiming priority to U.S. Provisional App. Ser. No. 60/325,424 filed on Sep. 25, 2001), the entire contents of which are expressly incorporated by reference as if set forth herein in their entirety ("the '424 PCT"). Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a split-dilator disposed within the initial dilator) is employed to distract the tissues extending between the skin of the patient and a given surgical target site (preferably along the posterior region of the target intervertebral disc). A secondary distraction assembly (i.e. a plurality of sequentially dilating cannulae) may optionally be employed after the initial distraction assembly to further distract the tissue. Once distracted, the resulting void or distracted region within the patient is of sufficient size to accommodate a tissue retraction assembly of the present invention. More specifically, the tissue retraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slideably engaged with the posterior retractor blade) may be advanced such that a distal shim extension in positioned within the posterior region of the disc space. If done before retraction, this helps ensure that the posterior retractor blade will not move posteriorly during the retraction process, even though the other retractor blades (i.e. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (i.e. nerves, vasculature, etc . . . ) into or out of the operative corridor. Once the operative corridor is established, any of a variety of surgical instruments, devices, or implants may be passed through and/or manipulated within the operative corridor depending upon the given surgical procedure.

FIG. 1 illustrates a tissue retraction assembly 10 forming part of a surgical access system according to the present invention. The retraction assembly 10 includes a plurality of retractor blades extending from a handle assembly 20. By way of example only, the handle assembly 20 is provided with a posterior retractor blade 12, a cephalad-most retractor blade 16, and a caudal-most retractor blade 18. Although shown and described below with regard to the three-bladed configuration, it is to be readily appreciated that the number of retractor blades may be increased or decreased without departing from the scope of the present invention. The retractor assembly 10 is shown in a fully retracted or "open" configuration, with the retractor blades 12, 16, 18 positioned a distance from one another so as to form an operative corridor 15 there between and extending to a surgical target site (i.e. an annulus of an intervertebral disc).

The retractor blades 12, 16, 18 may be equipped with various additional features or components. By way of example only, posterior retractor blade 12 may be equipped with a shim element 22 (shown more clearly in FIG. 15). Shim element 22 serves to distract the adjacent vertebral bodies (thereby restoring disc height), helps secure the retractor assembly 10 relative to the surgical target site, and forms a protective barrier to prevent the ingress or egress of instruments or biological structures (i.e. nerves, vasculature, etc . . . ) into or out of the operative corridor. Each of the remaining retractor blades (cephalad-most blade 16 and caudal-most blade 18) may be equipped with a retractor extender 24 (shown more clearly in FIG. 16). The retractor extenders 24 extend from the cephalad-most and caudal-most retractor blades 16, 18 to form a protective barrier to prevent the ingress or egress of instruments or biological structures (i.e. nerves, vasculature, etc . . . ) into or out of the operative corridor.

According to the present invention, any or all of the retractor blades 12, 16, 18, the shim element 22 and/or the retractor extender 24 may be provided with one or more electrodes 39 (preferably at their distal regions) equipped for use with a nerve surveillance system, such as, by way of example, the type shown and described in the NeuroVision PCT Applications set forth below.

The handle assembly 20 may be coupled to any number of mechanisms for rigidly registering the handle assembly 20 in fixed relation to the operative site, such as through the use of an articulating arm mounted to the operating table. The handle assembly 20 includes first and second arm members 26, 28 hingedly coupled via coupling mechanism 30 (i.e. bolt/nut combination disposed through receiving apertures formed along arm members 26, 28). The cephalad-most retractor blade 16 is rigidly coupled (generally perpendicularly) to the end of the first arm member 26. The caudal-most retractor blade 18 is rigidly coupled (generally perpendicularly) to the end of the second arm member 28. With combined reference to FIG. 10, the posterior retractor blade 12 is rigidly coupled (generally perpendicularly to) a translating member 17, which is coupled to the handle assembly 20 via a linkage assembly 14. The linkage assembly 14 includes a first link 34 hingedly disposed between the translating member 17 and a point along the first arm member 26 of the handle assembly 20, and a second link 36 hingedly disposed between the translating member 17 and the second arm member 28 of the handle assembly 20. The translating member 17 includes a translation slot 19 through the bolt/nut combination of the coupling mechanism 30 may engage. In use, a user can squeeze the proximal ends of the arms 26, 28 and thereby cause the coupling mechanism 30 to translate distally within the slot 19, which increases the relative distance between the posterior retractor blade 12 and the cephalad-most and caudal-most retractor blades 16, 18. This squeezing motion of the arms 26, 28 simultaneously causes the cephalad-most and caudal-most retractor blades 16, 18 to move away from one another. Taken collectively, the diameter of the operative corridor 15 increases at approximately the same time. An optional locking mechanism 35 (i.e. bolt and nut combination extending between arm members 26, 28) may be provided to selectively lock the arm members 26, 28 relative to one another to thus maintain the retractor assembly 10 in the fully retracted position, once achieved.

Figure 2:
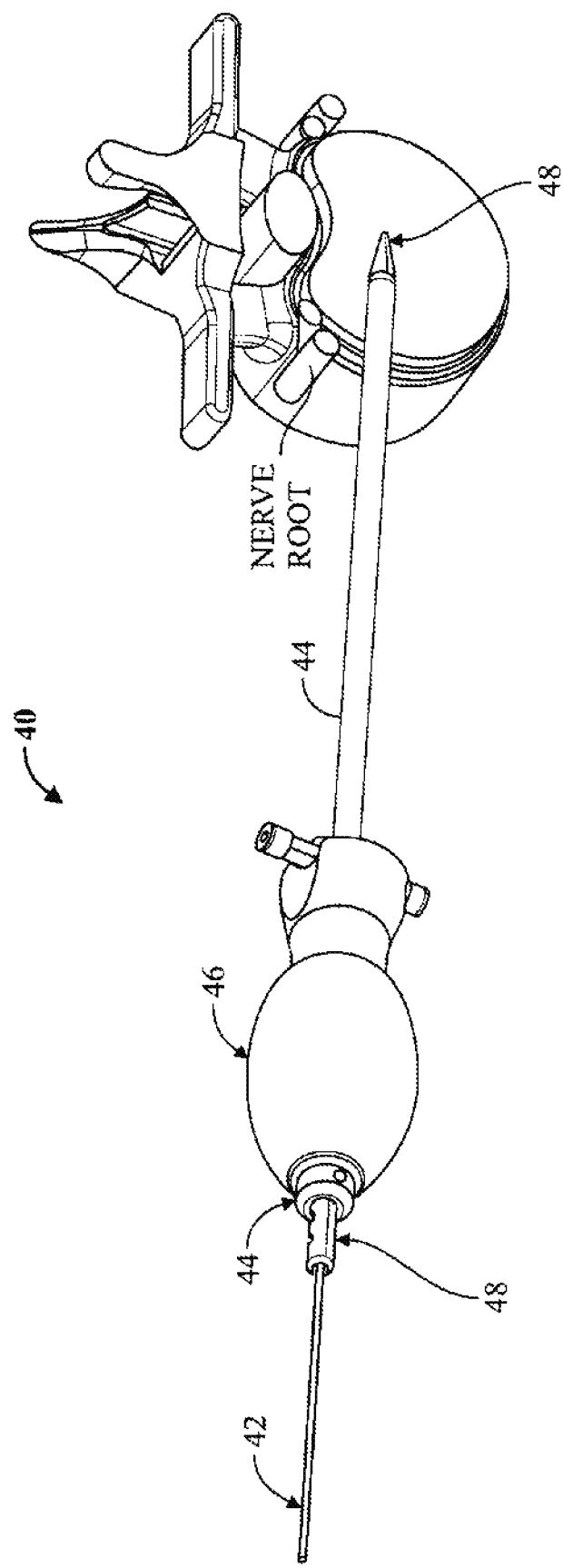
FIG. 2 is a perspective view illustrating the components and use of an initial distraction assembly (i.e. K-wire, an initial dilating cannula with handle, and a split-dilator housed within the initial dilating cannula) forming part of the surgical access system according to the present invention, for use in distracting to a surgical target site (i.e. annulus)
Figure 3:
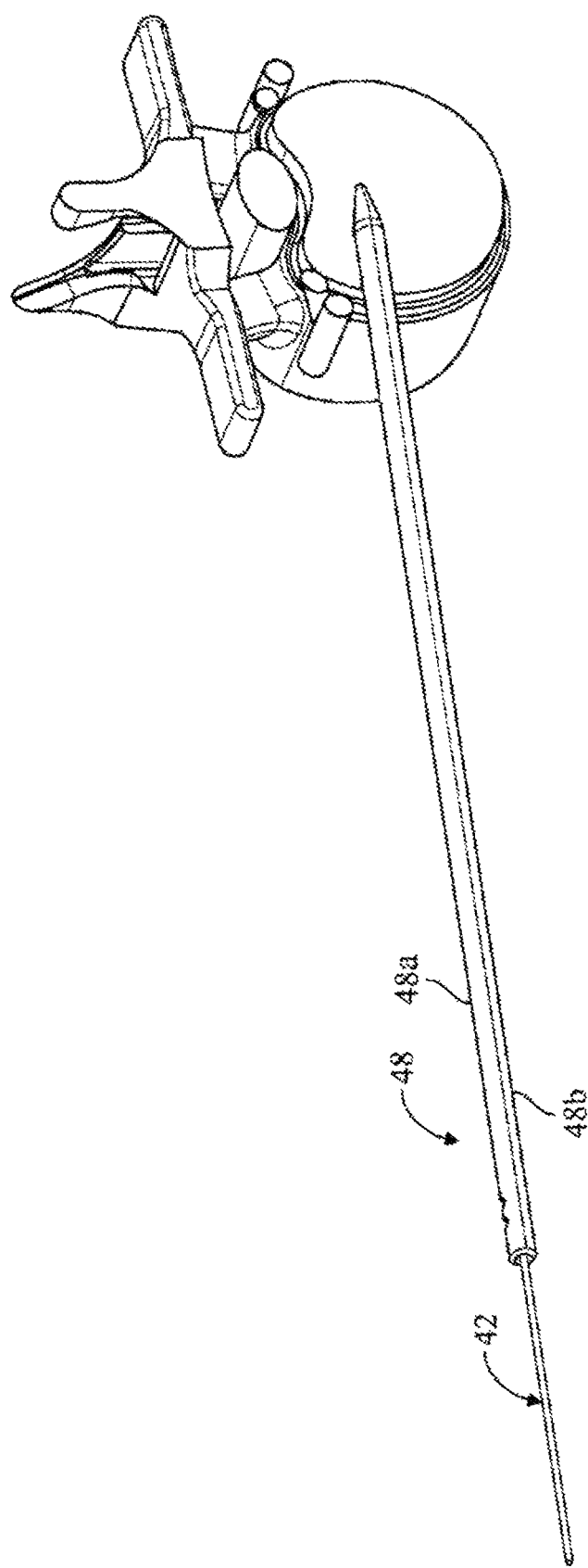
FIG. 3 is a perspective view illustrating the K-wire and split-dilator of the initial distraction assembly with the initial dilating cannula and handle removed.
Figure 4:
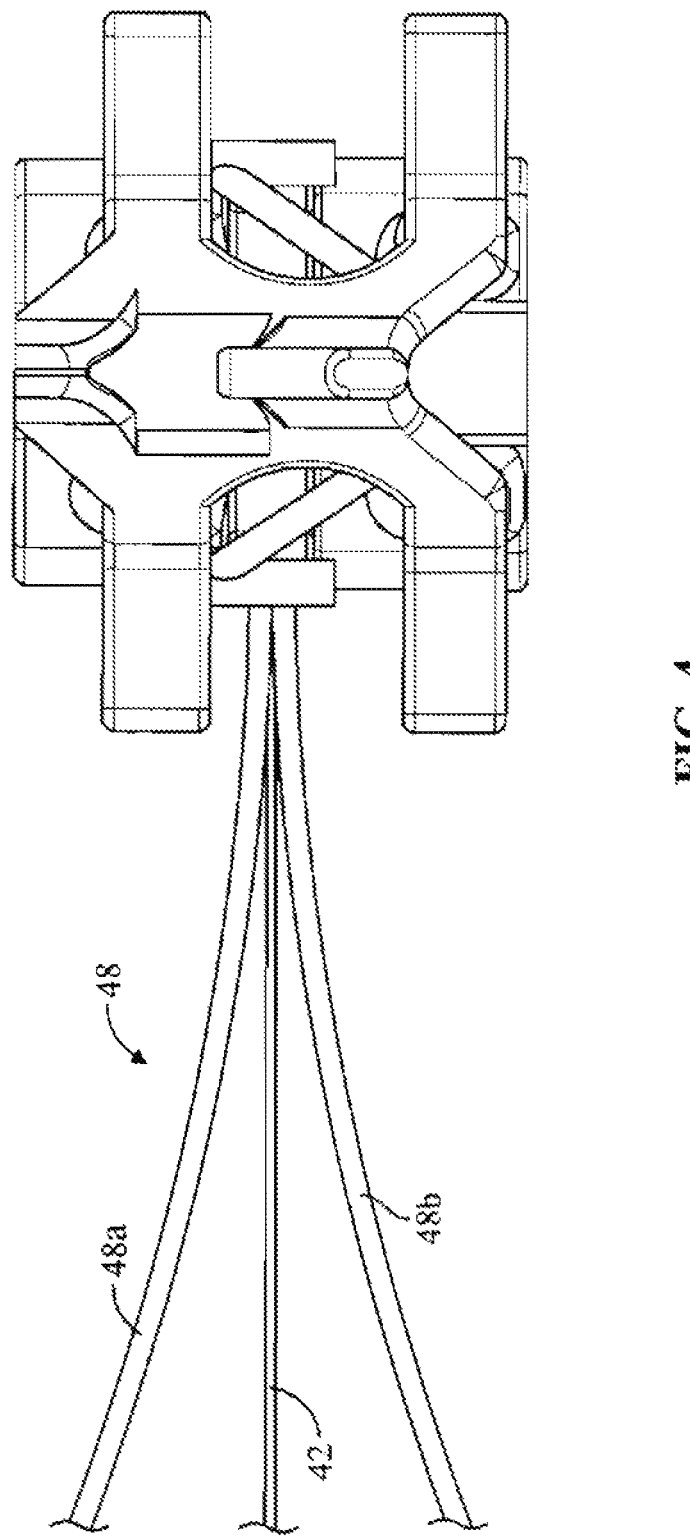
FIG. 4 is a posterior view of the vertebral target site illustrating the split-dilator of the present invention in use distracting in a generally cephalad-caudal fashion according to one aspect of the present invention.

FIG. 2 illustrates an initial distraction assembly 40 forming part of the surgical access system according to the present invention. The initial distraction assembly 40 includes a K-wire 42, an initial dilating cannula 44 with handle 46, and a split-dilator 48 housed within the initial dilating cannula 44. In use, the K-wire 42 and split-dilator 48 are disposed within the initial dilating cannula 44 and the entire assembly 40 advanced through the tissue towards the surgical target site (i.e. annulus). Again, this is preferably accomplished while employing the nerve detection and/or direction features described above. After the initial dilating assembly 40 is advanced such that the distal ends of the split-dilator 48 and initial dilator 44 are positioned within the disc space (FIG. 2), the initial dilator 44 and handle 46 are removed (FIG. 3) to thereby leave the split-dilator 48 and K-wire 42 in place. As shown in FIG. 4, the split-dilator 48 is thereafter split such that the respective halves 48a, 48b are separated from one another to distract tissue in a generally cephalad-caudal fashion relative to the target site. The split dilator 48 may thereafter be relaxed (allowing the dilator halves 48a, 48b to come together) and rotated such that the dilator halves 48a, 48b are disposed in the anterior-posterior plane. Once rotated in this manner, the dilator halves 48a, 48b are again separated to distract tissue in a generally anterior-posterior fashion. Each dilator halve 48a, 48b may be, according to the present invention, provided with one or more electrodes (preferably at their distal regions) equipped for use with a nerve surveillance system, such as, by way of example, the type shown and described in the NeuroVision PCT Applications set forth below.

Figure 5:
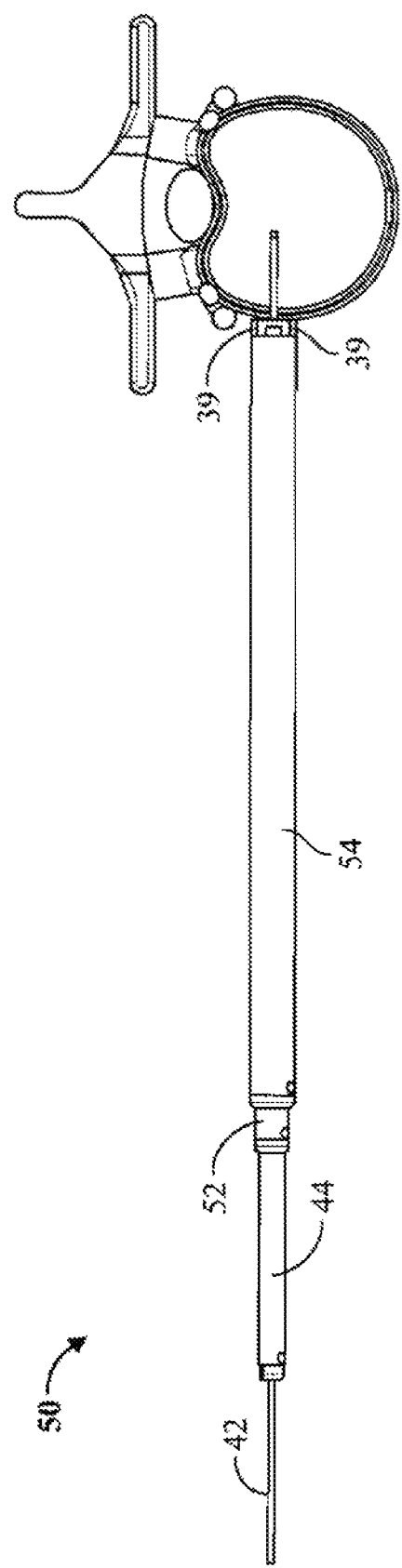
FIG. 5 is a side view illustrating the use of a secondary distraction assembly (comprising a plurality of dilating cannulae over the K-wire) to further distract tissue between the skin of the patient and the surgical target site according to the present invention.

Following this initial distraction, a secondary distraction may be optionally undertaken, such as via a sequential dilation system 50 as shown in FIG. 5. According to the present invention, the sequential dilation system 50 may include the K-wire 42, the initial dilator 44, and one or more supplemental dilators 52, 54 for the purpose of further dilating the tissue down to the surgical target site. Once again, each component of the secondary distraction assembly 50 (namely, the K-wire 42, the initial dilator 44, and the supplemental dilators 52, 54 may be, according to the present invention, provided with one or more electrodes (preferably at their distal regions) equipped for use with a nerve surveillance system, such as, by way of example, the type shown and described in the NeuroVision PCT Applications set forth below.

Figure 6:
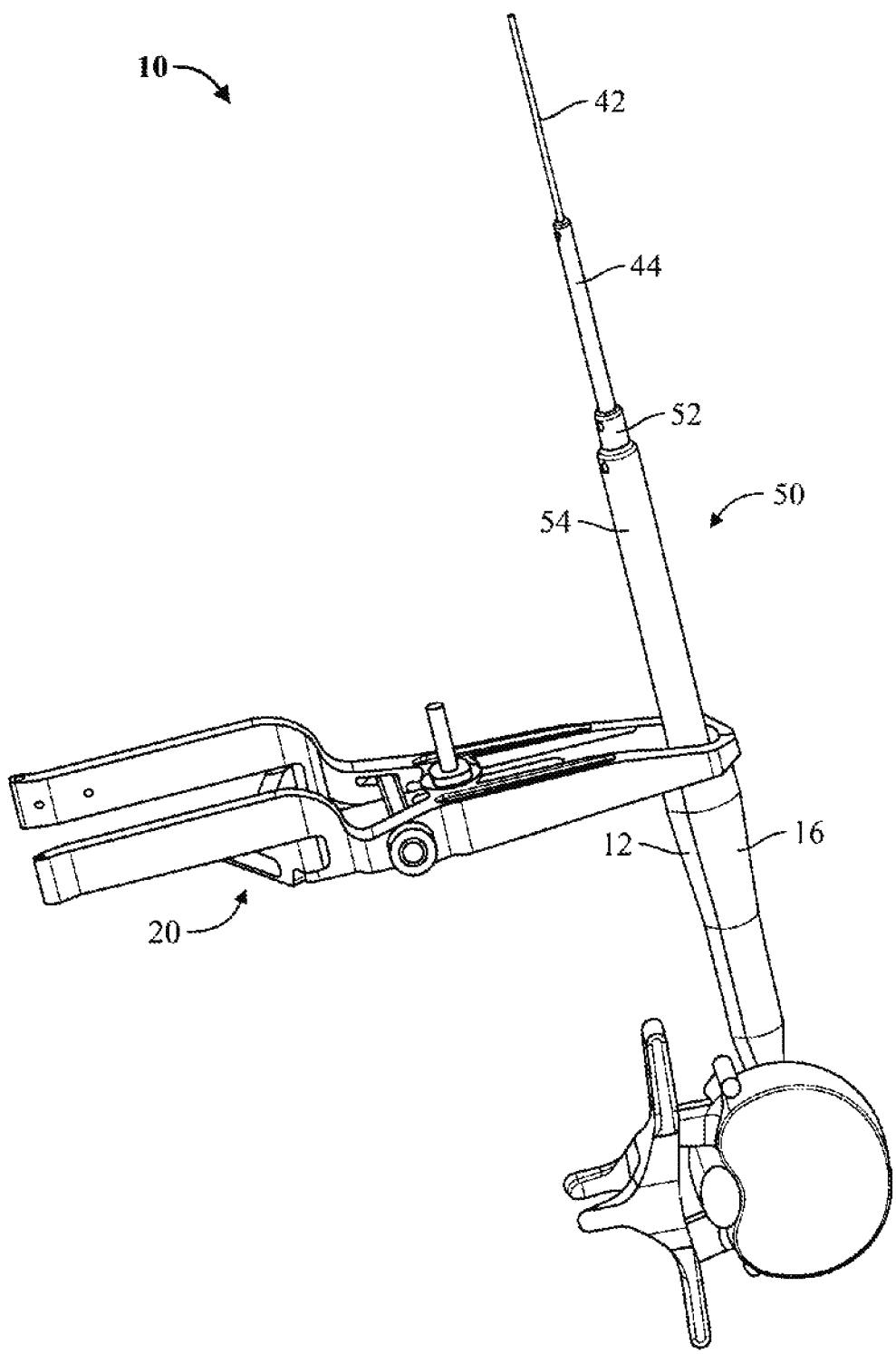
FIGS. 6-7 are perspective and side views, respectively, of a retractor assembly according to the present invention, comprising a handle assembly having three (3) retractor blades extending there from (posterior, cephalad-most, and caudal-most) disposed over the secondary distraction assembly of FIG. 5 (shown in a first, closed position)
Figure 7:
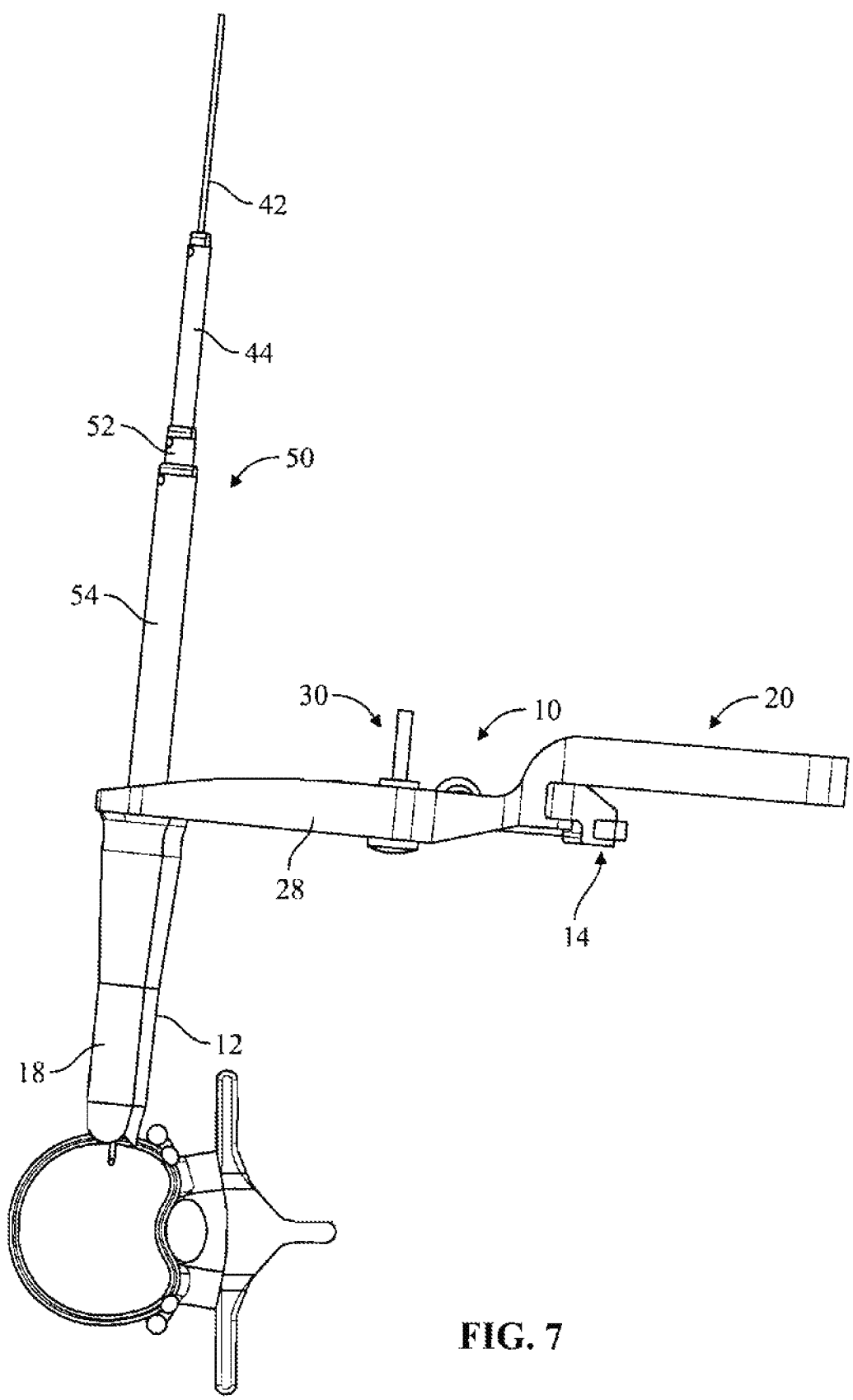
Figure 8:
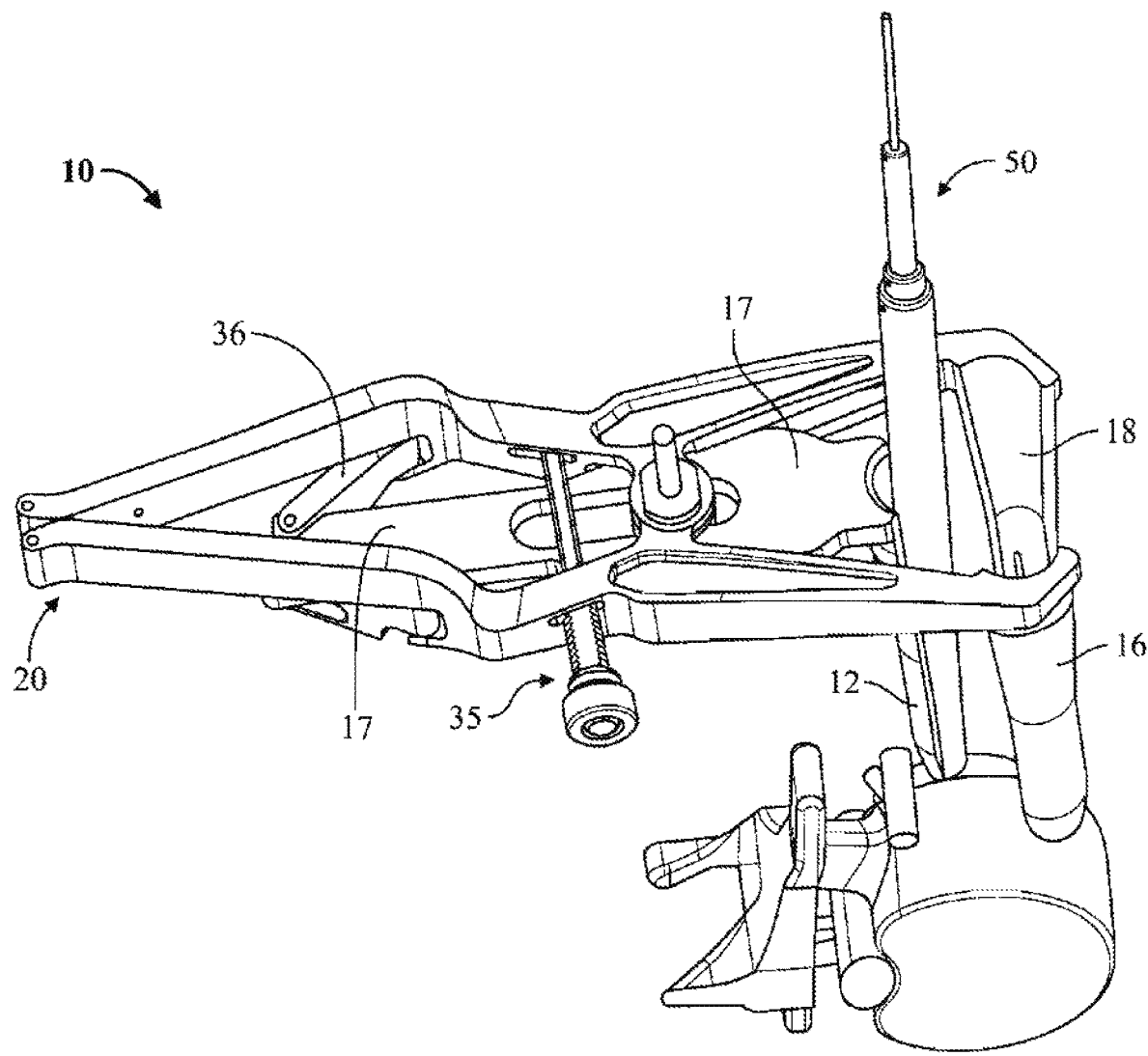
FIGS. 8-10 are perspective, side and top views, respectively, of the retractor assembly of FIGS. 6-7 in a second, opened (i.e. retracted) position (over the secondary distraction assembly) to thereby create an operative corridor to a surgical target site according to the present invention.
Figure 9:
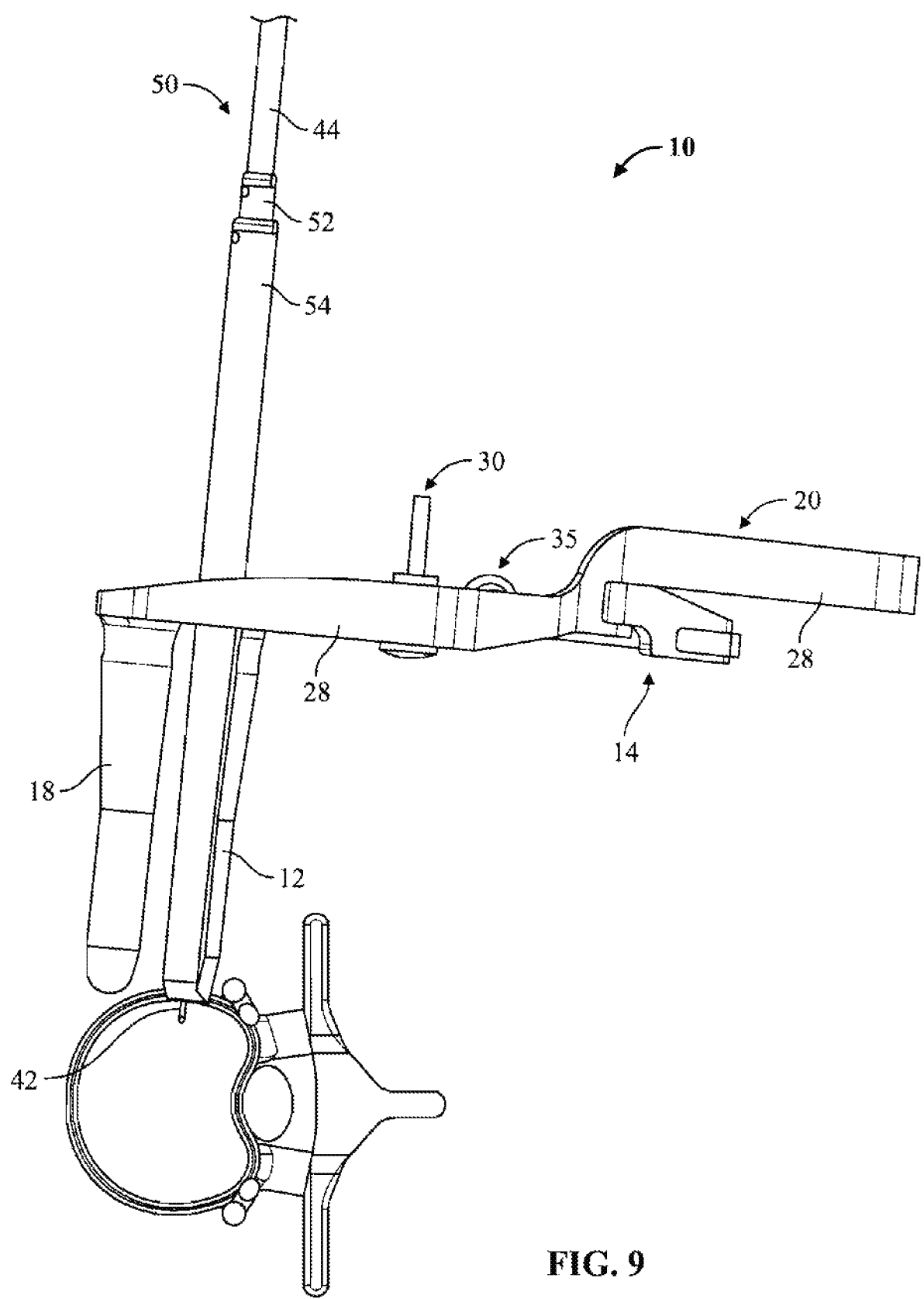
Figure 10:
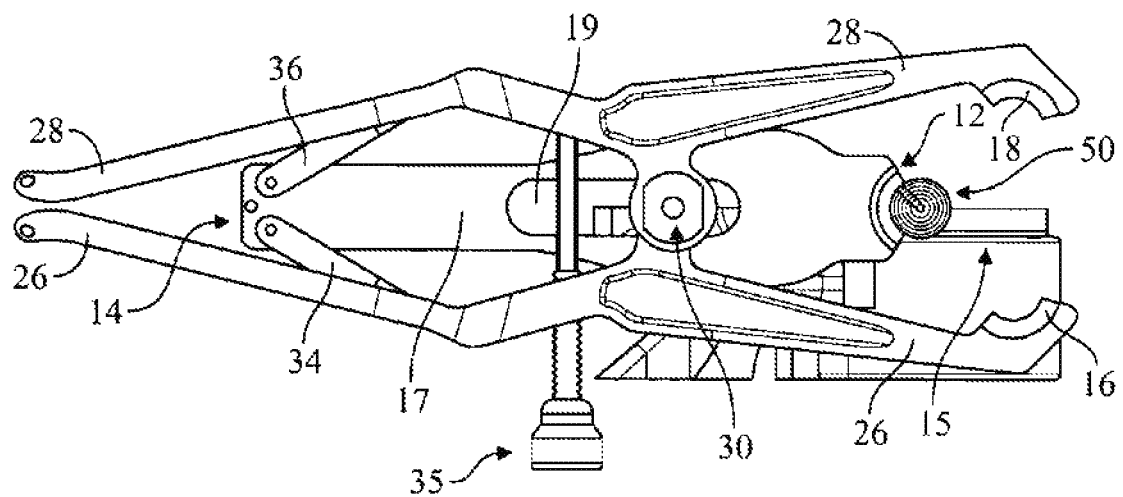
Figure 11:
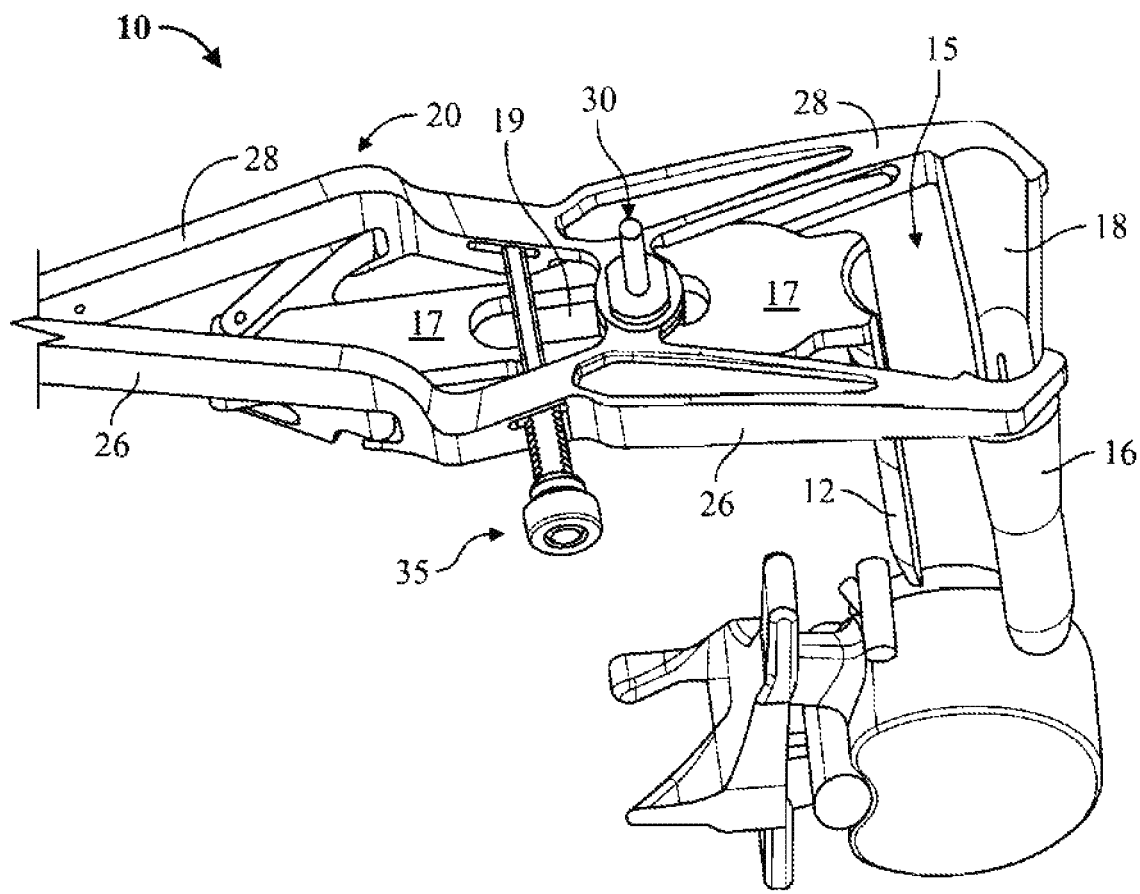
FIGS. 11-13 are perspective, side and top views, respectively, of the retractor assembly of FIGS. 6-7 in the second, opened (i.e. retracted) position (with the secondary distraction assembly removed) illustrating the operative corridor to the surgical target site according to the present invention.
Figure 12:
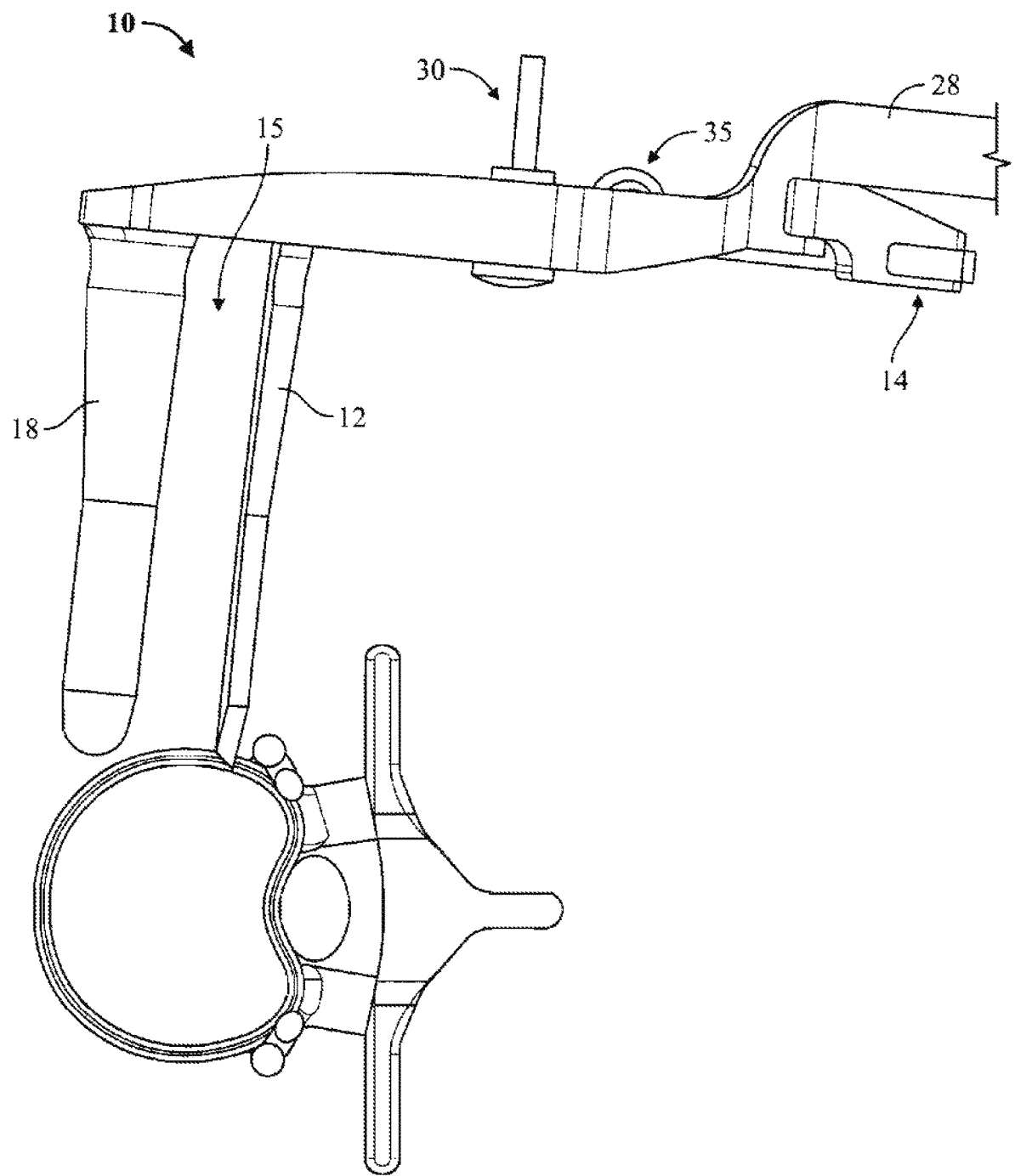
Figure 13:
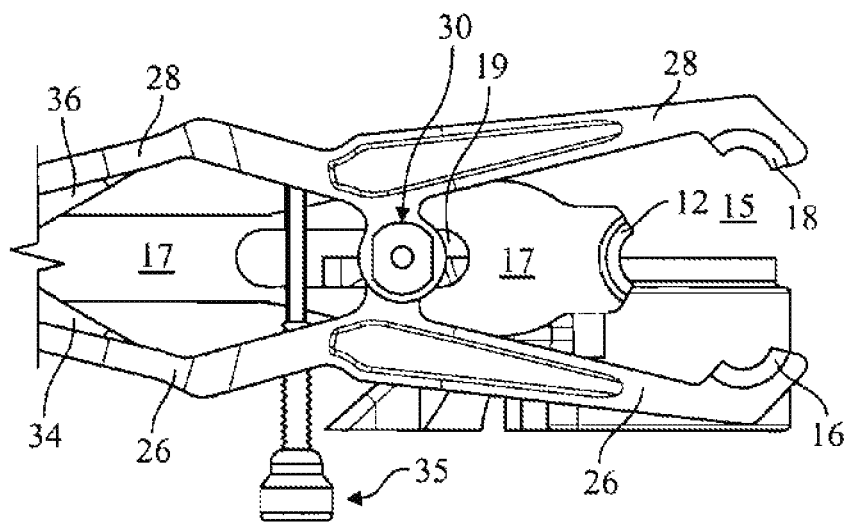

As shown in FIGS. 6-7, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another). Once advanced to the surgical target site, the handle assembly 20 may be operated as shown in FIGS. 8-10 to move the retractor blades 12, 16, 18 into a second, open or "retracted" position. As one can see, the posterior retractor blade 12 is allowed to stay in the same general position during this process, such that the cephalad-most and caudal-most retractor blades 14, 16 move away from the posterior retractor blade 12. Again, this is accomplished through the cooperation between the translation member 17 (attached to the posterior retractor blade 12) and the arms 26, 28 of the handle assembly 20 via the linkage assembly 14 and slot 19 in conjunction with the coupling mechanism 30. FIGS. 11-13 illustrate the retractor assembly 10 in the second, opened (i.e. retracted) position (with the secondary distraction assembly 50 removed for clarity) illustrating the operative corridor 15 to the surgical target site according to the present invention.

Figure 14:
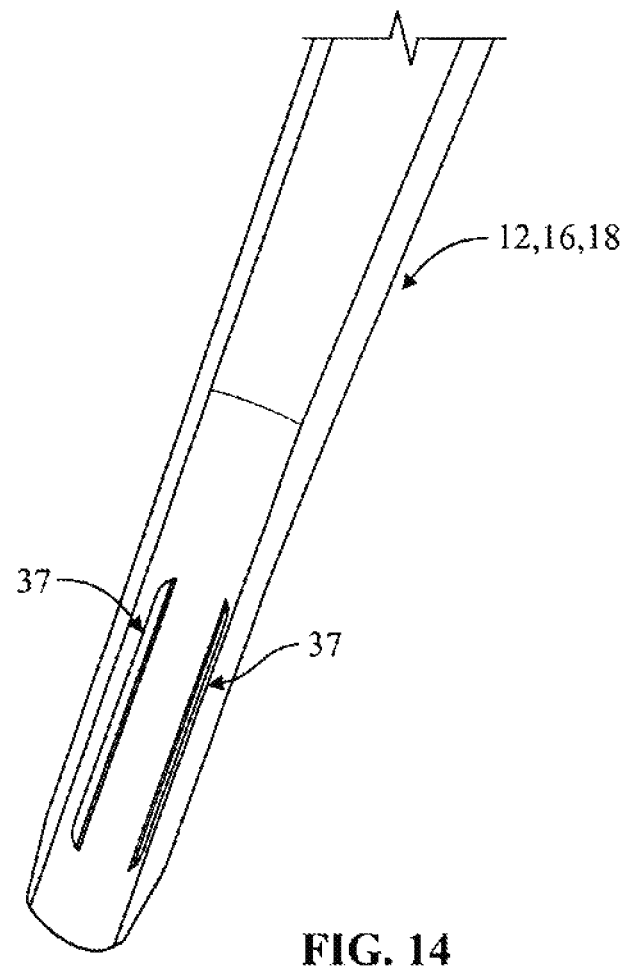
FIG. 14 is an enlarged perspective view of the interior surface of a retractor blade, illustrating a pair of dove-tail grooves dimensioned to engage a shim element (as shown in FIG. 15) and/or a retractor extender (as shown in FIG. 16) according to the present invention.
Figure 16:
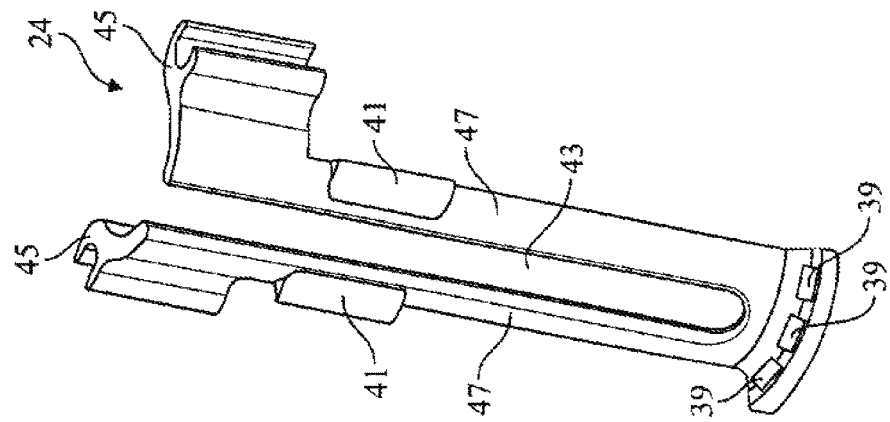
FIG. 16 is a perspective view of a retractor extender dimensioned to be adjustably and removably coupled to a retractor blade (as shown in FIG. 14) according to the present invention.
Figure 15:
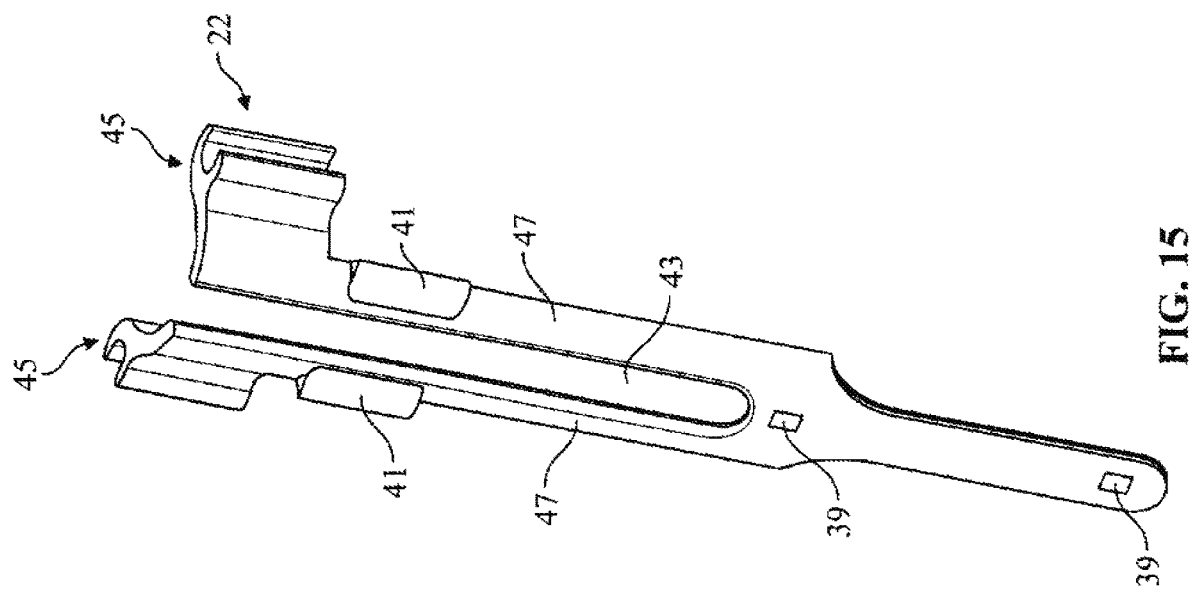
FIG. 15 is a perspective view of a shim element dimensioned to be adjustably and removably coupled to a retractor blade (as shown in FIG. 14) according to the present invention.
Figure 17:
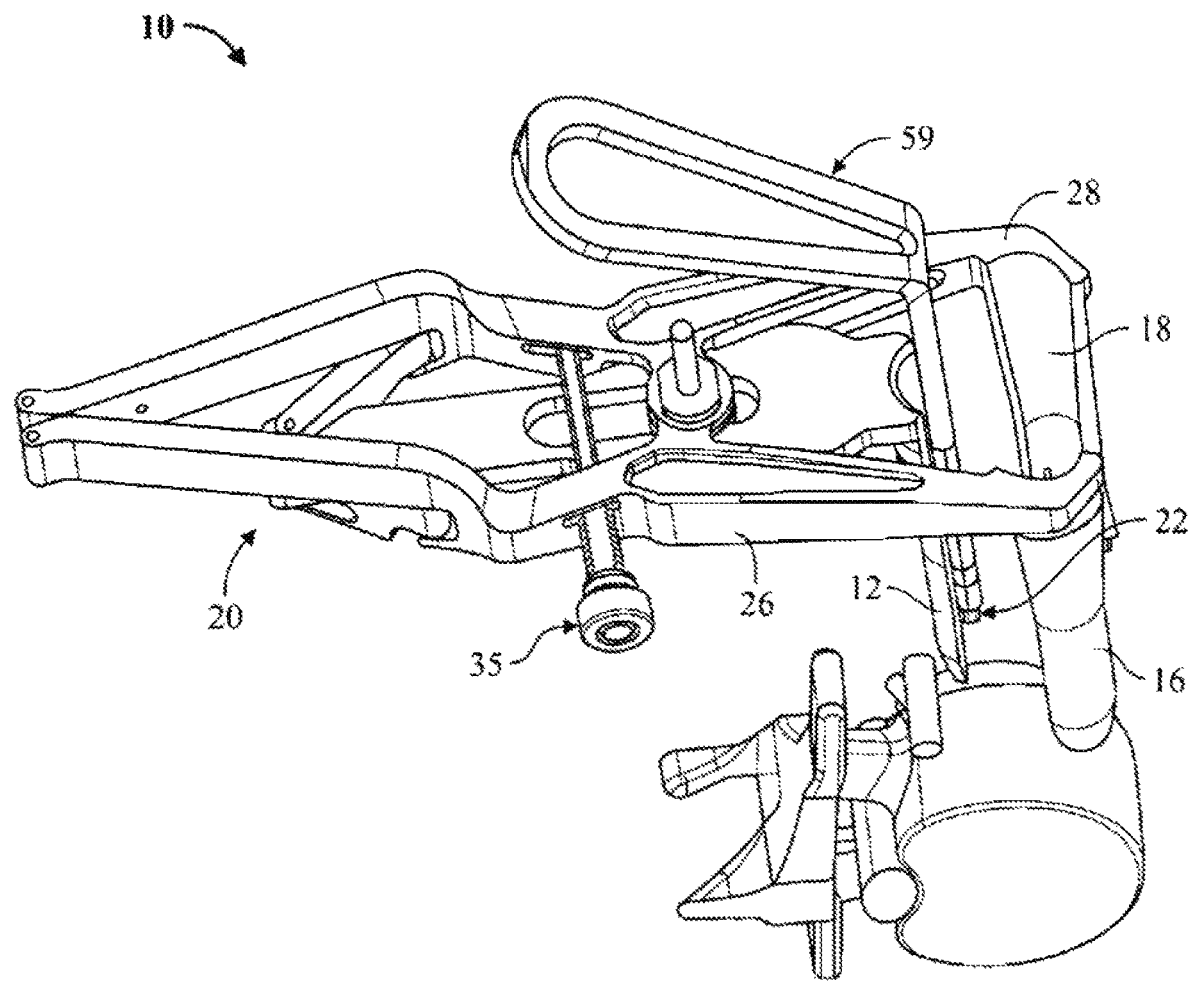
FIGS. 17-18 are perspective and side views, respectively, of the retractor assembly illustrating the use of an introducer device for coupling the shim element of FIG. 15 to the posterior retractor blade and introducing the distal end of the shim (shim extension) into the intradiscal space according to the present invention.
Figure 18:
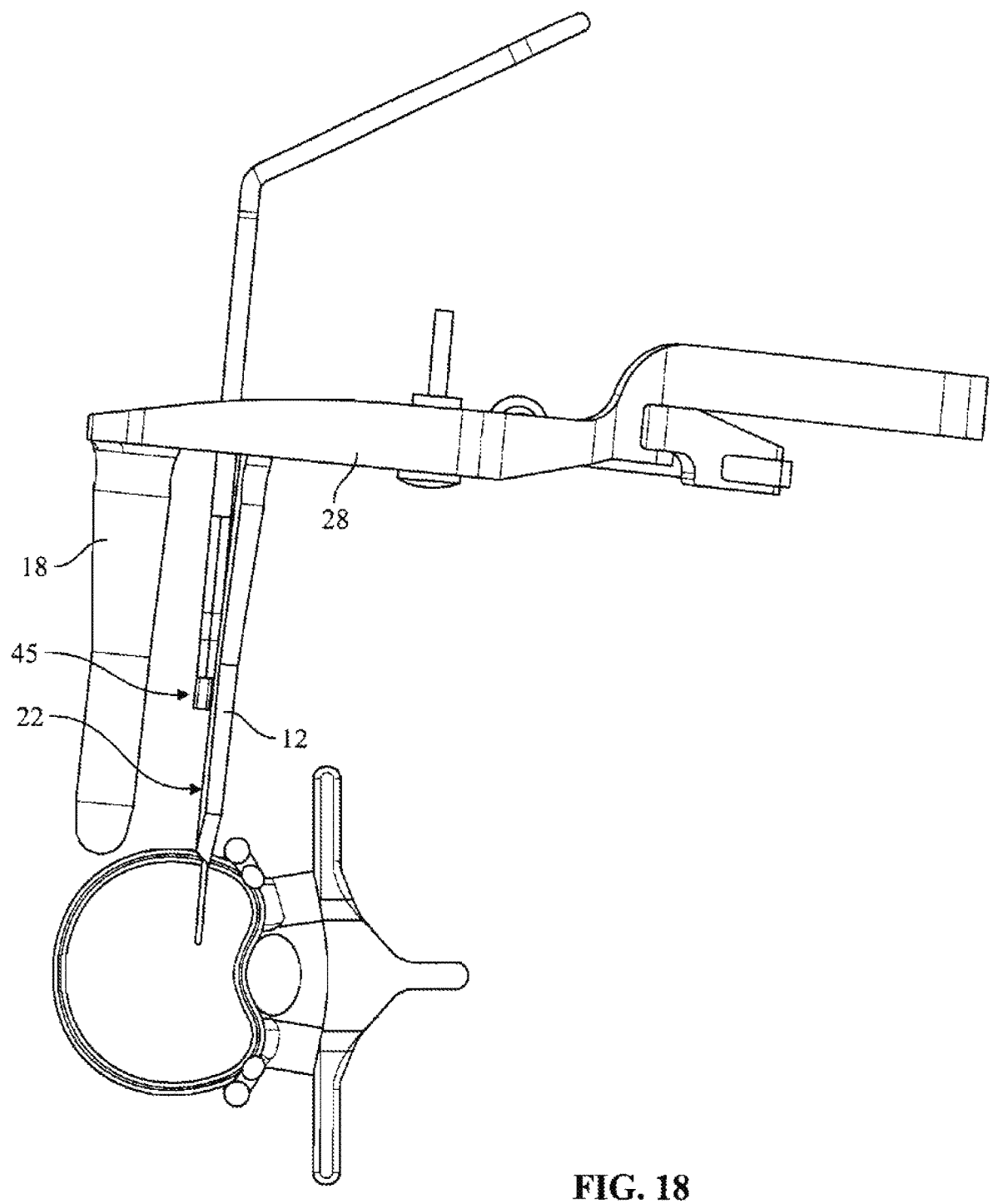
Figure 19:
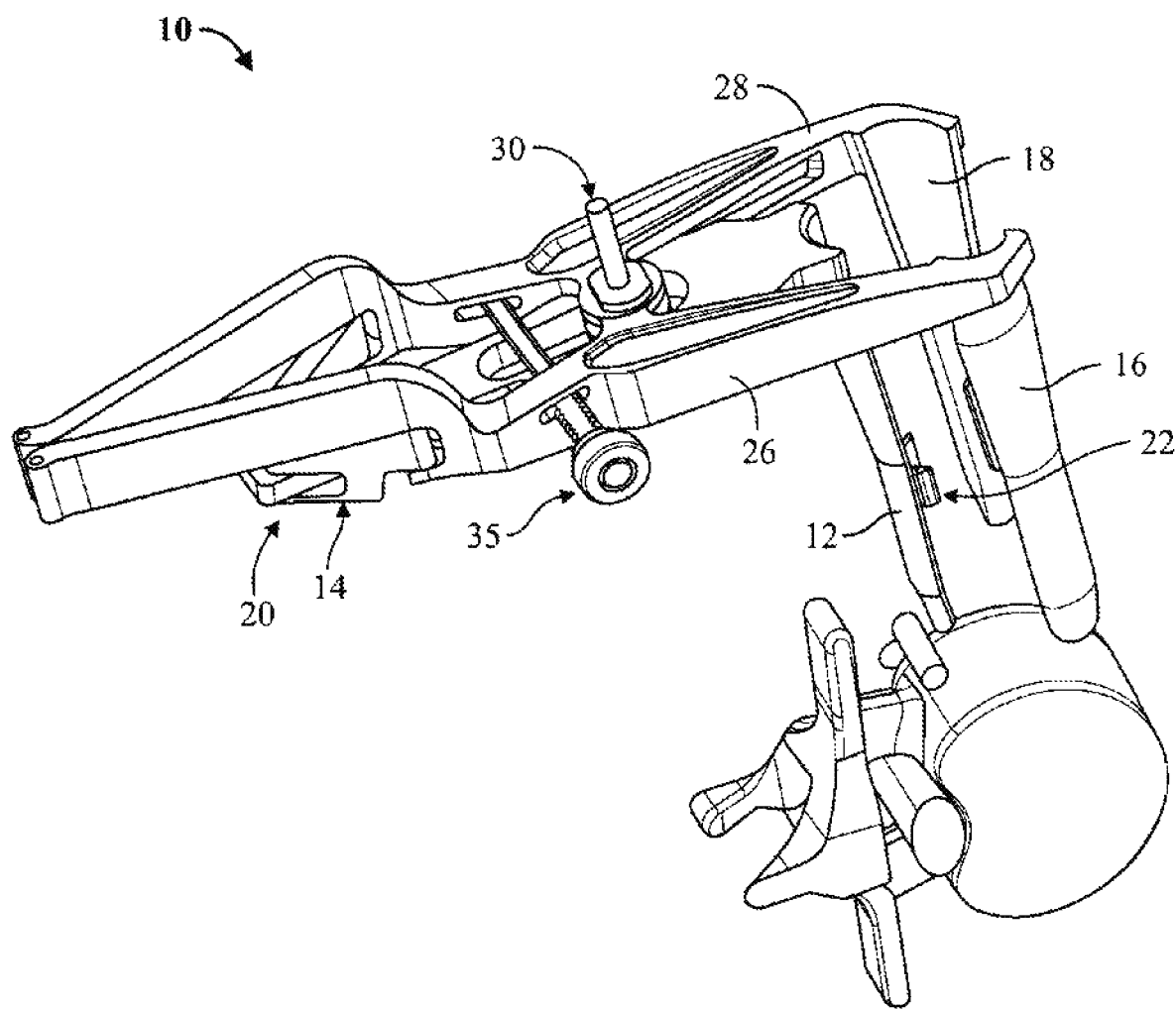
FIGS. 19-21 are perspective, side and top views, respectively, of the retractor assembly illustrating the shim element after introduction according to the present invention.
Figure 20:
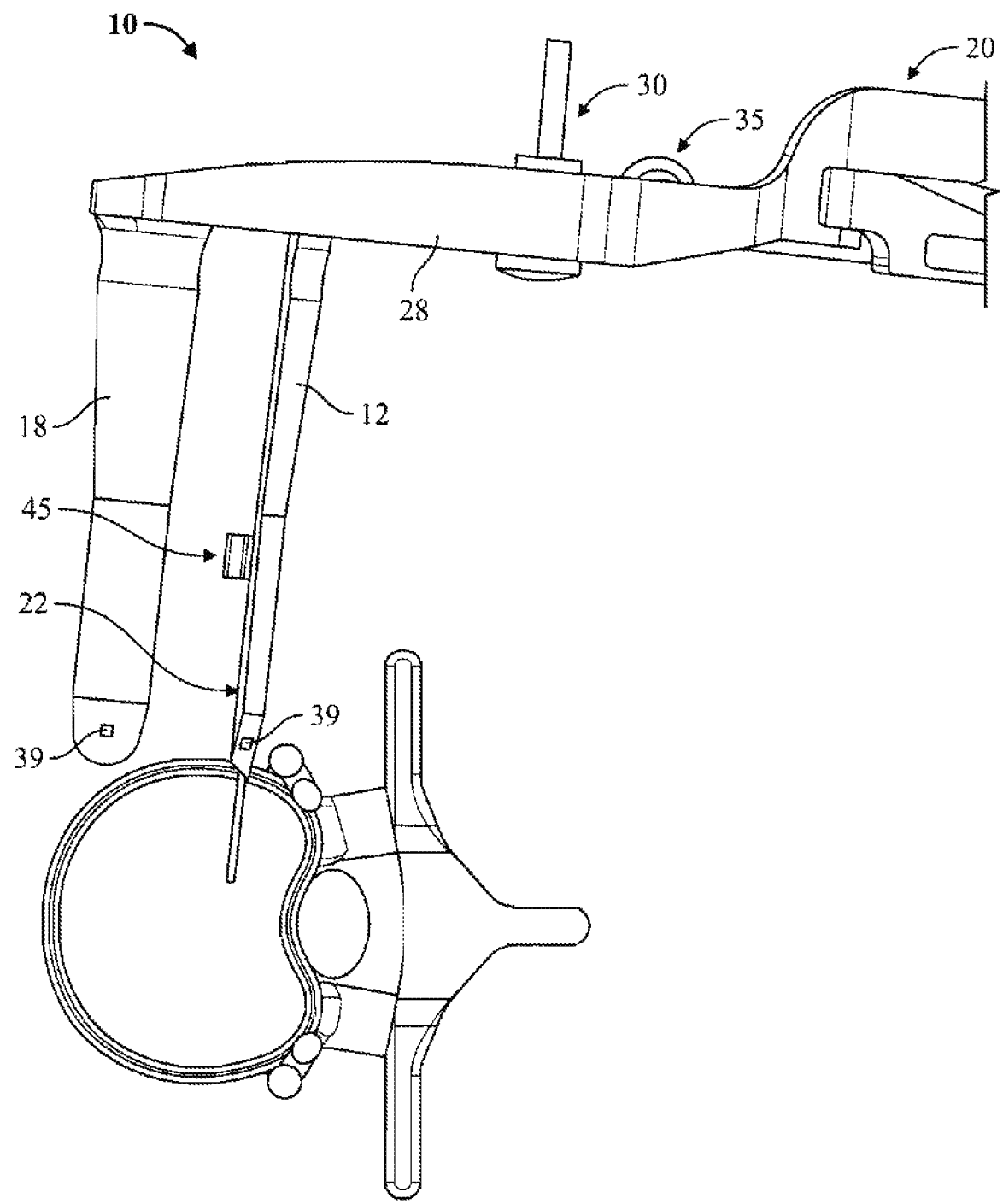
Figure 21:
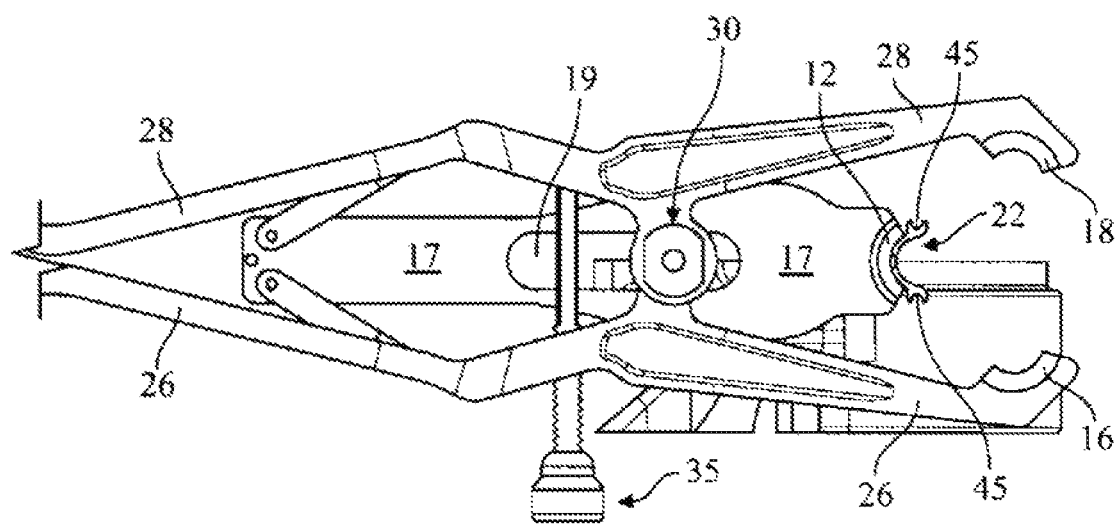
Figure 22:
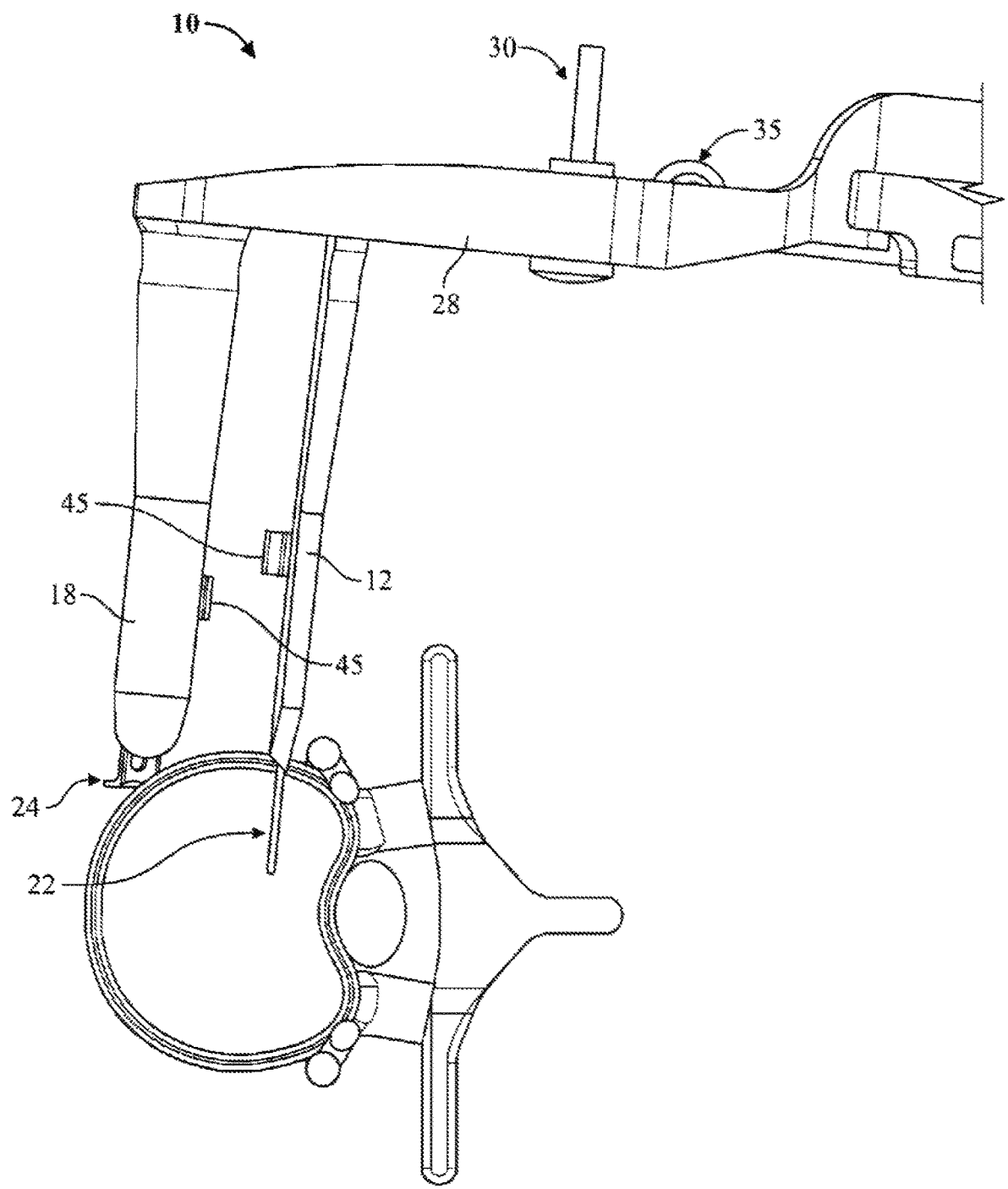
FIG. 22 is a side view of the retractor assembly illustrating the shim element and one of two retractor extenders after introduction according to the present invention.

FIGS. 14-16 illustrate an important aspect of the present invention, wherein (FIG. 15) each retractor blade 12, 16, 18 is provided with a pair of engagement grooves 37 having, by way of example only, a generally dove-tailed cross-sectional shape. The engagement grooves 37 are dimensioned to engage with dove-tail elements 41 provided on the shim element 22 (FIG. 15) and each retractor extender 24 (FIG. 16). In a preferred embodiment, the shim element 22 and retractor extender 24 are each provided with an elongate slot 43 and tool-engaging elements 45. A tool may be used to bias the arms 47 of each device inwardly towards one another (decreasing the width of part or most of the slot 43), which forces the dove-tail elements 41 towards one another. This is shown, by way of example only, in FIGS. 17-18, wherein a tool 59 is used to introduce the shim element 22 into engaged relation with the posterior retractor blade 12. When the shim element 22 has been introduced to a desired position (such as having the distal end extend into the intradiscal space as best shown in FIGS. 18 and 20), the tool 59 may then be disengaged or released from the tool-engaging elements 45 such that the dove-tail elements 41 return to their normal position (being biased outwardly by the resiliency of the arms 47) to thereby secure the shim element 22 relative to the posterior retractor blade 12. FIGS. 19-21 illustrate the shim element 22 after introduction according to the present invention. The same process can be used with the retractor extender 24 shown in FIG. 16 with respect to the cephalad-most and caudal-most retractor blades 16, 18. The end result is shown in FIG. 22 with the retraction assembly 10 of the present invention disposed in position over a surgical target site.

Nerve Surveillance

According to yet another aspect of the present invention, any number of distraction components and/or retraction components (including but not limited to those described herein) may be equipped to detect the presence of (and optionally the distance and/or direction to) neural structures during the steps tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist. Such monitoring may also be carried out via the surgeon-driven EMG monitoring system shown and described in the following commonly owned and co-pending PCT Applications (collectively "NeuroVision PCT Applications"): PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003. The entire contents of each of the above-enumerated NeuroVision PCT Applications is hereby expressly incorporated by reference into this disclosure as if set forth fully herein.

In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 23:
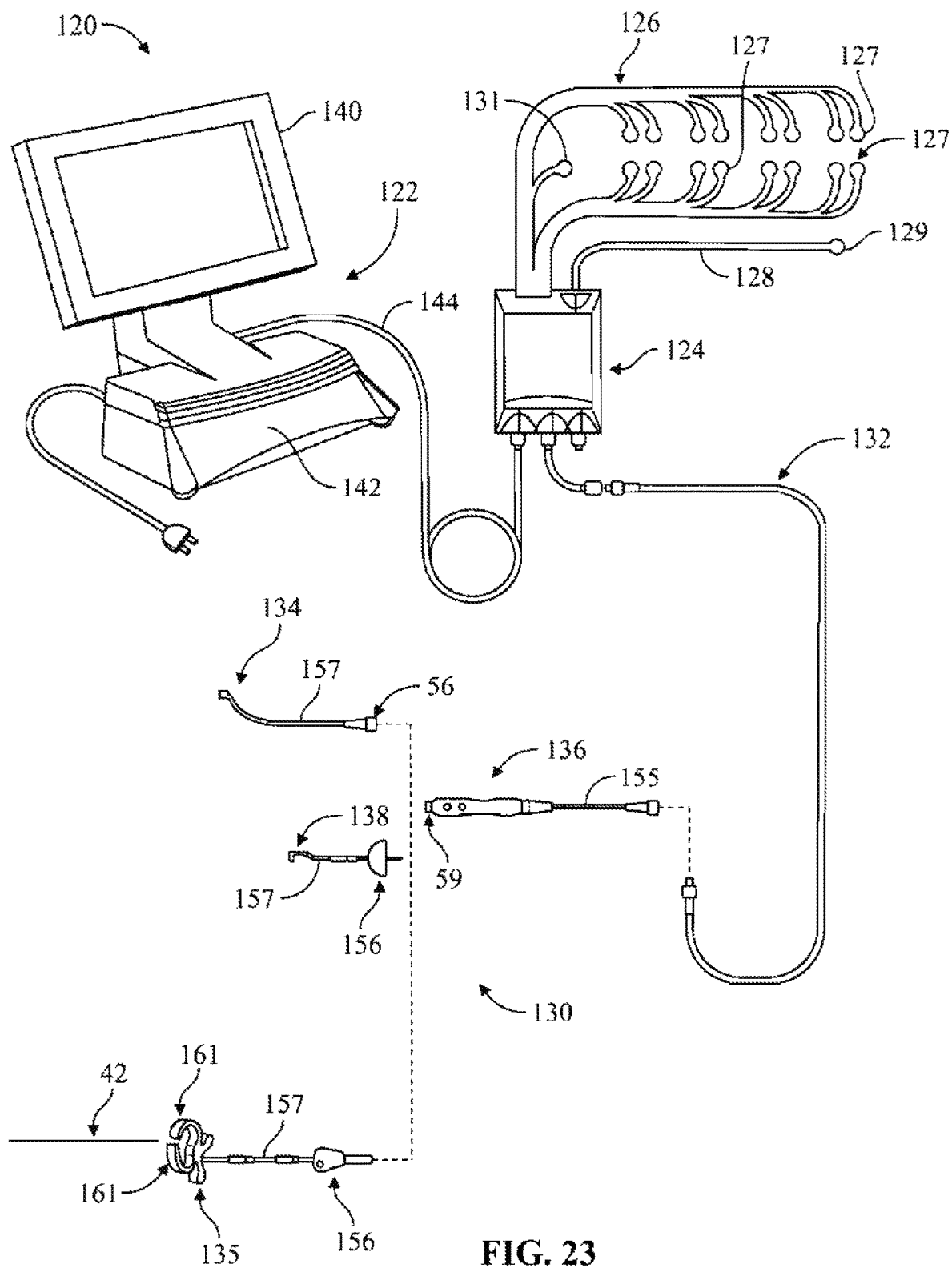
FIG. 23 is a perspective view of an exemplary nerve monitoring system capable of performing nerve monitoring before, during and after the creating of an operative corridor to a surgical target site using the surgical access system in accordance with the present invention.
Figure 24:
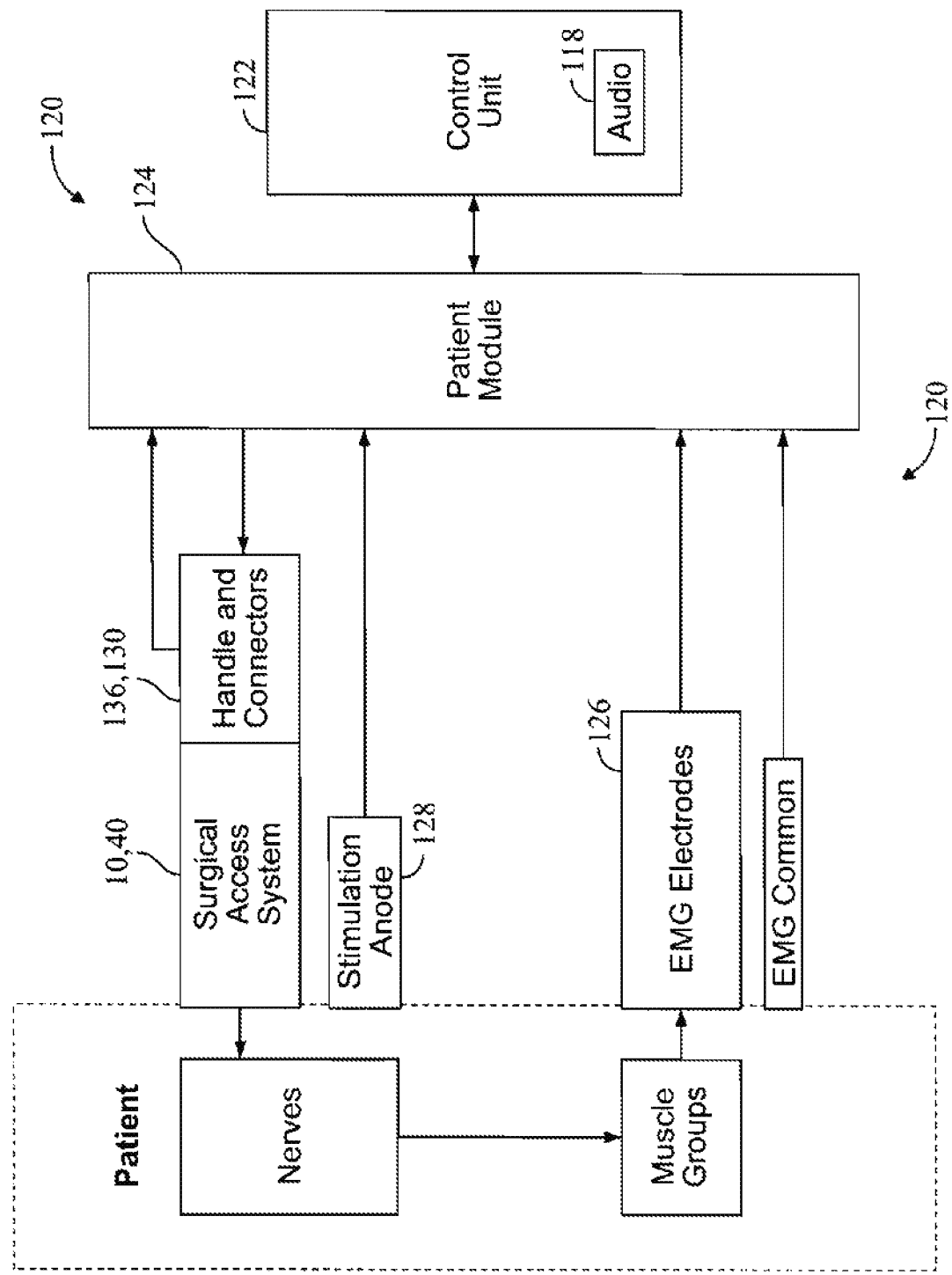
FIG. 24 is a block diagram of the nerve monitoring system shown in FIG. 23.

FIGS. 23-24 illustrate, by way of example only, a monitoring system 120 of the type disclosed in the NeuroVision PCT Applications suitable for use with the surgical access system 10 of the present invention. The monitoring system 120 includes a control unit 122, a patient module 124, and an EMG harness 126 and return electrode 128 coupled to the patient module 124, and a cable 132 for establishing electrical communication between the patient module 124 and the surgical access system 10 (FIG. 1). More specifically, this electrical communication can be achieved by providing, by way of example only, a hand-held stimulation controller 152 capable of selectively providing a stimulation signal (due to the operation of manually operated buttons on the hand-held stimulation controller 152) to one or more connectors 156a, 156b, 156c. The connectors 156a, 156b, 156c are suitable to establish electrical communication between the hand-held stimulation controller 152 and (by way of example only) the stimulation electrodes on the K-wire 42, the dilators 44, 52, 54, the retractor blades 12, 16, 18 and/or the shim elements 22, 24 (collectively "surgical access instruments").

In order to use the monitoring system 120, then, these surgical access instruments must be connected to the connectors 156a, 156b and/or 156c, at which point the user may selectively initiate a stimulation signal (preferably, a current signal) from the control unit 122 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a surgical element with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions. The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one embodiment, the monitoring system 120 is capable of determining nerve direction relative to one or more of the surgical access instruments before, during and/or following the creation of an operative corridor to a surgical target site. Monitoring system 120 accomplishes this by having the control unit 122 and patient module 124 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 25:
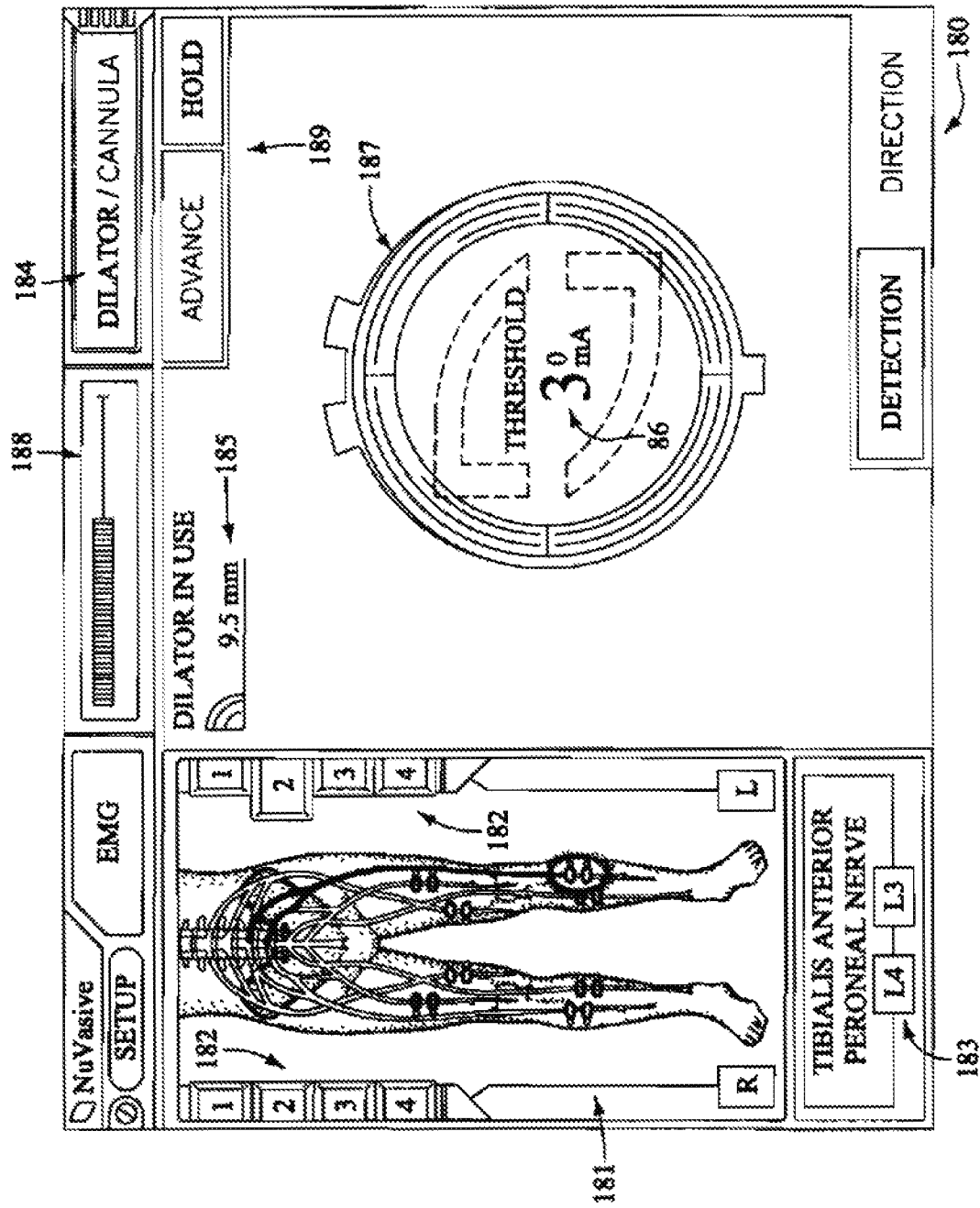
FIGS. 25-26 are screen displays illustrating exemplary features and information communicated to a user during the use of the nerve monitoring system of FIG. 23.
Figure 26:
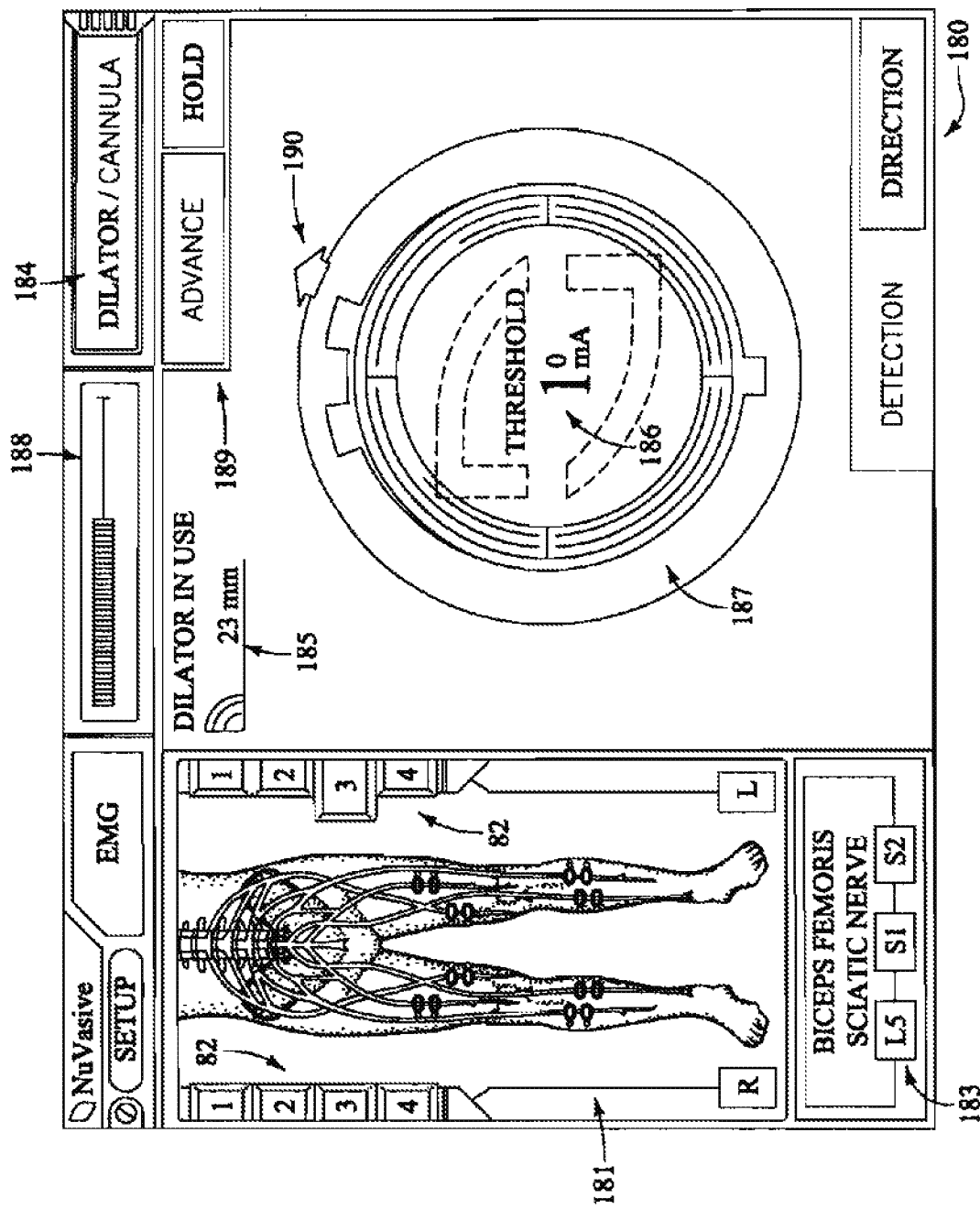

FIGS. 25-26 are exemplary screen displays (to be shown on the display 140) illustrating one embodiment of the nerve direction feature of the monitoring system shown and described with reference to FIGS. 23-24. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (in this case, a dilator 46, 48), the size of the instrument being used 185, the stimulation threshold current 186, a graphical representation of the instrument being used 187 (in this case, a cross-sectional view of a dilator 46, 48) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 15) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various instruments forming the surgical access system 10 of the present invention, including the distraction assemblies 40, 50, the retractor blades 12, 16, 18 and/or the shim members 22, 24.

The surgical access system 10 of the present invention may be sold or distributed to end users in any number of suitable kits or packages (sterile and/or non-sterile) containing some or all of the various components described herein.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction of bone products (such as allograft or autograft) and/or devices having ceramic, metal and/or plastic construction (such as mesh) and/or compounds such as bone morphogenic protein), total disc replacement, etc . . . ).

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

While certain embodiments have been described, it will be appreciated by those skilled in the art that variations may be accomplished in view of these teachings without deviating from the spirit or scope of the present application. For example, with regard to the monitoring system 120, it may be implemented using any combination of computer programming software, firmware or hardware. As a preparatory act to practicing the system 120 or constructing an apparatus according to the application, the computer programming code (whether software or firmware) according to the application will typically be stored in one or more machine readable storage mediums such as fixed (hard) drives, diskettes, optical disks, magnetic tape, semiconductor memories such as ROMs, PROMs, etc., thereby making an article of manufacture in accordance with the application. The article of manufacture containing the computer programming code may be used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present application is not limited by the scope of the appended claims.

The invention claimed is:

1. A system for accessing a surgical target site, the system comprising:
   a three-bladed tissue retraction assembly comprising:
   a first retractor arm having a first length extending between a first proximal end and a first distal end and defining a first top surface, a first bottom surface, a first inner surface, and a first outer surface, wherein the first retractor arm comprises a first coupling portion extending laterally inward from first inner surface, wherein the first retractor arm defines a first hole extending laterally through the first retractor arm from the first outer surface to the first inner surface, and wherein the first coupling portion and the first hole are positioned along the first retractor arm between the first proximal end and the first distal end such that the first hole is positioned nearer the first proximal end and the first coupling portion is positioned nearer the first distal end;
   a second retractor arm having a second length extending between a second proximal end and a second distal end and defining a second top surface, a second bottom surface, a second inner surface, and a second outer surface, wherein the second retractor arm comprises a second coupling portion extending laterally inward from second inner surface, wherein the second retractor arm defines a second hole extending laterally through the second retractor arm from the second outer surface to the second inner surface, and wherein the second coupling portion and the second hole are positioned along the second retractor arm between the second proximal end and the second distal end such that the second hole is positioned nearer the second proximal end and the second coupling portion is positioned nearer the second distal end;
   a translating retractor member having a third length extending between a third proximal end and a third distal end, wherein the first retractor arm is pivotably connected with respect to the translating retractor member via the first coupling portion and the second retractor arm is pivotably connected with respect to the translating retractor member via the second coupling portion such that the first and second retractor arms can pivot with respect to the translating retractor member and the translating retractor member can translate with respect to the first and second retractor arms;
   a caudal-most retractor blade coupled to the first retractor arm;
   a cephalad-most retractor blade coupled to the second retractor arm;
   a posterior-most retractor blade coupled to the translating retractor member;
   an intradiscal shim element that releasably mounts to the posterior-most retractor blade such that a maximum length of the intradiscal shim element extends generally parallel to a maximum length of the posterior-most retractor blade and a tip portion of the intradiscal shim element extends from the posterior-most retractor blade, wherein the intradiscal shim element engages with a groove defined by the posterior-most retractor blade to penetrate into a spinal disc at the targeted spinal site when the intradiscal shim element is releasably mounted to the posterior-most retractor blade; and
   a mechanism comprising a bolt extending through at least one of the first and second holes so as to selectively position the first retractor arm with respect to the second retractor arm.

2. The system of claim 1, wherein the mechanism is a locking mechanism configured to lock the first and second retractor arms in a retracted position once the first and second retractor arms are placed in the retracted position.

3. The system of claim 1, wherein the first retractor arm has a first extension extending between the first hole and the first proximal end of the first retractor arm and the second retractor arm has a second extension extending between the second hole and the second proximal end of the second retractor arm.

4. The system of claim 1, wherein the mechanism turns about a first axis, wherein the first retractor arm pivots about a second axis that extends through the first coupling portion, and wherein the first axis is perpendicular to the second axis.

5. The system of claim 1, and further comprising:
a sequential dilation system comprising a plurality of dilators sized for the three-bladed tissue retraction assembly to be advanced over the sequential dilation system, wherein each of the plurality of dilators has at least one stimulation electrode at distal regions of the plurality of dilators, and wherein each of the caudal-most retractor blade, cephalad-most retractor blade, and posterior-most retractor blade has at least one stimulation electrode at distal regions of the caudal-most retractor blade, cephalad-most retractor blade, and posterior-most retractor blade; and
a nerve surveillance system electrically connectable to each of the dilators and retractor blades and configured to stimulate the dilators and retractor blades when inserted into tissue proximate nerves.

6. The system of claim 5, wherein each of the caudal-most retractor blade, cephalad-most retractor blade, and posterior-most retractor blade has at least one stimulation electrode at distal regions thereof.

7. The system of claim 1, wherein the three-bladed retraction assembly is configured to maintain a trans-psoas operative corridor to the surgical target site at a lumbar spine, the system further comprising means for trans-psoas dilation to define a tissue distraction corridor.

8. The system of claim 7, wherein the means for trans-psoas dilation comprises a sequential dilation system configured to advance through a psoas muscle to define the tissue distraction corridor.

9. The system of claim 8, wherein the sequential dilation system comprises a plurality of dilators sized for the tissue retraction assembly to be advanced over the sequential dilation system.

10. The system of claim 7, wherein the means for trans-psoas dilatation comprises at least one stimulation electrode at a distal region so as to output electrical stimulation within a psoas muscle.

11. The system of claim 1, wherein the first and second retractor arms pivot about a common axis.

12. A system for accessing a surgical target site, the system comprising:
a three-bladed tissue retraction assembly comprising:
a first retractor arm having a first length extending between a first proximal end and a first distal end and defining a first top surface, a first bottom surface, a first inner surface, and a first outer surface, wherein the first retractor arm comprises a first coupling portion extending laterally inward from first inner surface, wherein the first retractor arm defines a first hole extending laterally through the first retractor arm from the first outer surface to the first inner surface, and wherein the first coupling portion and the first hole are positioned along the first retractor arm between the first proximal end and the first distal end such that the first hole is positioned nearer the first proximal end and the first coupling portion is positioned nearer the first distal end;
a second retractor arm having a second length extending between a second proximal end and a second distal end and defining a second top surface, a second bottom surface, a second inner surface, and a second outer surface, wherein the second retractor arm comprises a second coupling portion extending laterally inward from second inner surface, wherein the second retractor arm defines a second hole extending laterally through the second retractor arm from the second outer surface to the second inner surface, and wherein the second coupling portion and the second hole are positioned along the second retractor arm between the second proximal end and the second distal end such that the second hole is positioned nearer the second proximal end and the second coupling portion is positioned nearer the second distal end;
a third retractor member having a third length extending between a third proximal end and a third distal end, wherein the first retractor arm is pivotably connected with respect to the third retractor member via the first coupling portion and the second retractor arm is pivotably connected with respect to the third retractor member via the second coupling portion such that the first and second retractor arms can pivot with respect to the third retractor member;
a caudal-most retractor blade coupled to the first retractor arm;
a cephalad-most retractor blade coupled to the second retractor arm;
a posterior-most retractor blade coupled to the third retractor member;
an intradiscal shim element that releasably mounts to the posterior-most retractor blade such that a maximum length of the intradiscal shim element extends generally parallel to a maximum length of the posterior-most retractor blade and a tip portion of the intradiscal shim element extends from the posterior-most retractor blade, wherein the intradiscal shim element engages with a groove defined by the posterior-most retractor blade to penetrate into a spinal disc at the targeted spinal site when the intradiscal shim element is releasably mounted to the posterior-most retractor blade;
a first link connected between the first retractor arm and the third retractor member such that the first link is pivotably connected to the third retractor member; and
a second link connected between the second retractor arm and the third retractor member such that the second link is pivotably connected to the third retractor member.

13. The system of claim 12, wherein the third retractor member comprises a single, continuous structure between the third proximal end and the third distal end.

14. The system of claim 12, wherein the first retractor arm pivots with respect to the third retractor member about a first axis extending through the first coupling portion, wherein the first link pivots with respect to the third retractor member about a second axis that is parallel to the first axis.

15. The system of claim 12, wherein the first link is connected to the first retractor arm at a location between the first proximal end and the first coupling portion and the second link is connected to the second retractor arm at a location between the second proximal end and the second coupling portion.

16. A system for accessing a surgical target site, the system comprising:
a three-bladed tissue retraction assembly comprising:
a first retractor arm having a first length extending between a first proximal end and a first distal end and defining a first top surface, a first bottom surface, a first inner surface, and a first outer surface, wherein the first retractor arm comprises a first coupling portion extending laterally and rigidly inward from the first inner surface, wherein the first retractor arm defines a first hole extending laterally through the first retractor arm from the first outer surface to the first inner surface, and wherein the first coupling portion and the first hole are positioned along the first retractor arm between the first proximal end and the first distal end such that the first hole is positioned nearer the first proximal end and the first coupling portion is positioned nearer the first distal end;
a second retractor arm having a second length extending between a second proximal end and a second distal end and defining a second top surface, a second bottom surface, a second inner surface, and a second outer surface, wherein the second retractor arm comprises a second coupling portion extending laterally and rigidly inward from the second inner surface, wherein the second retractor arm defines a second hole extending laterally through the second retractor arm from the second outer surface to the second inner surface, and wherein the second coupling portion and the second hole are positioned along the second retractor arm between the second proximal end and the second distal end such that the second hole is positioned nearer the second proximal end and the second coupling portion is positioned nearer the second distal end;
a translating retractor member having a third length extending between a third proximal end and a third distal end, wherein the first retractor arm is pivotably connected with respect to the translating retractor member via the first coupling portion and the second retractor arm is pivotably connected with respect to the translating retractor member via the second coupling portion such that the first and second retractor arms can pivot with respect to the translating retractor member and the translating retractor member can translate with respect to the first and second retractor arms;
a caudal-most retractor blade coupled to the first retractor arm;
a cephalad-most retractor blade coupled to the second retractor arm;
a posterior-most retractor blade coupled to the translating retractor member;
an intradiscal shim element that releasably mounts to the posterior-most retractor blade such that a maximum length of the intradiscal shim element extends generally parallel to a maximum length of the posterior-most retractor blade and a tip portion of the intradiscal shim element extends from the posterior-most retractor blade, wherein the intradiscal shim element engages with a groove defined by the posterior-most retractor blade to penetrate into a spinal disc at the targeted spinal site when the intradiscal shim element is releasably mounted to the posterior-most retractor blade;
a first link connected between the first retractor arm and the translating retractor member such that the first link is pivotably connected to the translating retractor member;
a second link connected between the second retractor arm and the translating retractor member such that the second link is pivotably connected to the translating retractor member; and
a mechanism comprising a bolt extending through at least one of the first and second holes so as to selectively position the first retractor arm with respect to the second retractor arm.

* * * * *